United States Patent [19]

Matsumura et al.

[11] Patent Number: 5,043,459

[45] Date of Patent: Aug. 27, 1991

[54] SACCHAROASCORBIC ACID DERIVATIVES AND PRODUCTION THEREOF

[75] Inventors: Koichi Matsumura, Ibaraki; Yoshihiro Sugihara, Toyonaka; Yoshiaki Shimizu, Nishinomiya; Kouichi Iida, Suita; Toshiro Yamashita, Toyono, all of Japan

[73] Assignee: Takeda Chemical Industries, Ltd., Osaka, Japan

[21] Appl. No.: 473,154

[22] Filed: Jan. 31, 1990

[30] Foreign Application Priority Data

Jan. 31, 1989 [JP] Japan .................................. 1-23481
Jan. 31, 1989 [JP] Japan .................................. 1-23482
Jan. 31, 1989 [JP] Japan .................................. 1-23483

[51] Int. Cl.$^5$ ................... C07D 307/62; A61K 31/34
[52] U.S. Cl. ................................. 549/315; 548/317; 546/214; 540/480; 540/596; 252/407; 514/473
[58] Field of Search .................... 549/315; 548/517; 546/214; 540/480, 596

[56] References Cited

U.S. PATENT DOCUMENTS 2,428,438 10/1947 Trenner .............................. 260/344
2,483,251 9/1949 Trenner ............................ 260/344.5
4,837,020 6/1989 Mise et al. ............................ 424/68

FOREIGN PATENT DOCUMENTS 0228273 7/1987 European Pat. Off. ............ 549/315
62-228092 10/1987 Japan .................................. 549/315
1-100186 4/1989 Japan .................................. 549/315
WO88/10256 12/1988 PCT Int'l Appl. .................. 549/315

OTHER PUBLICATIONS

Noller, "Chemistry of Organic Compounds" 2nd Ed. (1957) (Saunders) pp. 244-245, 278.
Kosai et al., Chem. Abstr., vol. 97, No. 7, Aug. 16, 1982, p. 631, Abstract No. 55611h.
Bayeyeno-Volant et al., Chem. Abstr., vol. 105, No. 4, Jul. 28, 1986, Abstract No. 33320u.
Stuber et al., Carbohydrate Research, 60 (1978), pp. 251-258.
Takamura et al., Vitamins, 56(3) pp. 117-131 (1982).

Primary Examiner—Robert T. Bond
Attorney, Agent, or Firm—Wenderoth, Lind & Ponack

[57] ABSTRACT

This invention relates to novel saccharoascorbic acid derivatives and their production. The derivatives are represented by the general formula set forth below, for example, an amido, a thioester or carboxylic ester of saccharoascorbic acid, and their salts.

The compounds of the present invention are useful for food additives as antioxidants, an intermediate for the production of dichiral compounds and medicines having antithrombotic activity.

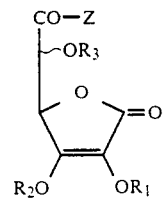

wherein Z represents

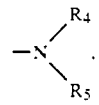

—$SR_6$ or —$OR_7$, $R_4$ and $R_5$ independently represent hydrogen or a hydrocarbon group of 1 to 24 carbon atoms, or $R_4$ and $R_5$ may together form $+CH_2+_n$ in which n is an integer of 4 to 7, $R_6$ represents a hydrocarbon group of 1 to 24 carbon atoms, $R_7$ represents hydrogen or a hydrocarbon group of 1 to 24 carbon atoms, $R_1$, $R_2$ and $R_3$ independently represent hydrogen, an acyl group of 1 to 18 carbon atoms or a hydrocarbon group of 1 to 24 carbon atoms, and ~ represents the R-configration or the S-configration; provided that when Z is —$OR_7$, $R_1$ and $R_2$ are not the same and $R_3$ is hydrogen, or a salt thereof.

24 Claims, No Drawings

SACCHAROASCORBIC ACID DERIVATIVES AND PRODUCTION THEREOF

This invention relates to novel saccharoascorbic acid derivatives and a method for their production.

The saccharoascorbic acid derivatives can be used as intermediates for production of the dichiral compounds, which are intermediates for liquid crystal compounds.

In another aspect, the novel compounds have antithrombotic activity. They can be used as medicines. The compounds promote fibrinolysis activity by contacting with endothelial cell etc. In view of this activity, the compounds are useful for prophylaxis and treatment of thrombosis (Japanese Patent Application No. 109789/1989).

The saccharoascorbic acid derivatives, which have at least one hydroxyl group at the 2- and/or 3-position, also have antioxidative activity. They are very useful for food additives as an antioxidant.

In more detail, this invention relates to derivatives of D-glucosaccharoascorbic acid (D-erythro-hex-2-enaro-1,4-lactone) or L-gulosaccharoascorbic acid (L-threo-hex-2-enaro-1,4-lactone) represented by the formula

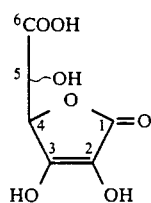

(I)

wherein the 2-, 3- and/or 5-hydroxyl groups and 6-carboxyl group have been converted to derivatives, or their salts, and a method for their production.

In the above formula, ~OH represents the isomeric forms; when the hydroxyl group is located on the right side (absolute configration R), the formula represents L-gulosaccharoascorbic acid, when located on the left side (absolute configration S), the formula represents D-glucosaccharoascorbic acid.

Similarly, in the saccharoascorbic acid derivatives as well, the right and left sides respectively represent the R- and S-absolute configrations.

BACKGROUND OF THIS INVENTION

L-ascorbic acid, erythorbic acid, their derivatives and L-gulosaccharoascorbic acid [U.S. Pat. Nos. 2,428,438 and 2,483,251; Carbohydrate Research, 60, 251–258 (1978); Vitamin, 56, 117–131 (1982)] are known as compounds possessing antioxidative activity.

Also, the present inventors synthesized D-glucosaccharoascorbic acid (European Patent Laid-open No. 228,273) and various esters of L-gulosaccharoascorbic acid and D-glucosaccharoascorbic acid (European Patent Laid-open No. 295,842).

DETAILED DESCRIPTION OF THIS INVENTION

Within the framework of the research into compounds related to ascorbic acid possessing antioxidative activity, the present inventors conducted investigations on the synthesis of various derivatives of L-gulosaccharoascorbic acids and D-glucosaccharoascorbic acid, and unexpectively found that derivatives of these saccharoascorbic acids and their salts are new compounds possessing antioxidative activity and antithrombotic activity.

The present inventors conducted further investigations on the production of these compounds, and firmly established a method for their production.

The novel compounds of the present invention can be represented by the formula

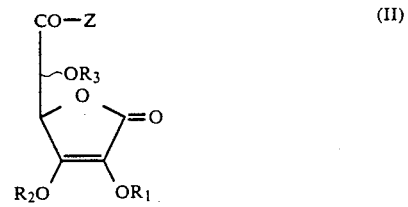

(II)

wherein Z represents

$-SR_6$ or $-OR_7$, $R_4$ and $R_5$ independently represent hydrogen or a hydrocarbon group of 1 to 24 carbon atoms, or $R_4$ and $R_5$ may together form $-(CH_2)_n-$ in which n is an integer of 4 to 7, $R_6$ represents a hydrocarbon group of 1 to 24 carbon atoms, $R_7$ represents hydrogen or a hydrocarbon group of 1 to 24 carbon atoms, $R_1$, $R_2$ and $R_3$ independently represent hydrogen, an acyl group of 1 to 18 caron atoms or a hydrocarbon group of 1 to 24 carbon atoms, and ~ represents the R-configration or the S-configration; provided that when Z is $-OR_7$, $R_1$ and $R_2$ are not the same and $R_3$ represents a hydrogen, or a salt thereof.

Examples of the hydrocarbon group of 1 to 24 carbon atoms for $R_1$, $R_2$, $R_3$, $R_4$, $R_5$, $R_6$ and $R_7$ include normal or branched alkyl groups, cycloalkyl groups, alkenyl groups, alkynyl groups, aralkyl groups and aryl groups.

Examples of the normal or branched alkyl group of 1 to 24 carbon atoms include methyl, ethyl, n-propyl, iso-propyl, n-butyl, sec-butyl, tert-butyl, n-pentyl, iso-amyl, tert-amyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-oactadecyl, n-eicosyl, n-docosyl, n-tetracosyl, etc. These groups may further have a substituent such as a halogen (e.g., fluorine, chlorine, iodine, bromine), nitro, cyano, hydroxyl, carboxyl or an ester (e.g., a lower alkyl ester), aminocarbonyl, acyl (e.g., a lower alkanoyl), alkoxy of 1 to 4 carbon atoms, etc.

Examples of the cycloalkyl group include those of 3 to 8 carbon atoms e.g., cyclopropyl, cyclobutyl, cyclopentyl, cyclohexyl, cycloheptyl, cyclooctyl, etc. These groups may further have a substituent such as a halogen (e.g., fluorine, chlorine, iodine, bromine), nitro, cyano, hydroxyl, carboxyl or an ester thereof (e.g., a lower alkyl ester), aminocarbonyl, acyl (e.g., a lower alkanoyl), alkoxy of 1 to 4 carbon atoms, alkyl of 1 to 4 carbon atoms, etc.

Examples of the alkenyl group of 2 to 24 carbon atoms include vinyl, allyl, butenyl, pentenyl, hexenyl, heptenyl, octenyl, nonenyl, decenyl, undecenyl, dodecenyl, tridecenyl, tetradecenyl, pentadecenyl, heptadecenyl, octadecenyl, nonadecenyl, eicosenyl, etc. These groups may further have a substituent such as a halogen (e.g., fluorine, chlorine, iodine, bromine), nitro, cyano, hydroxyl, carboxyl or an ester thereof (e.g., a lower alkyl ester), aminocarbonyl, acyl (e.g., a lower alkanoyl), alkoxy of 1 to 4 carbon atoms, etc.

Examples of the alkynyl group of 2 to 24 carbon atoms include ethynyl, propynyl, butynyl, pentynyl, hexynyl, heptynyl, octynyl, nonynyl, decynyl, undecynyl, dodecynyl, tridecynyl, tetradecynyl, pentadecynyl, heptadecynyl, octadecynyl, nonadecynyl, eicosynyl, etc. These groups may further have a substituent such as a halogen (e.g., fluorine, chlorine, iodine, bromine), nitro, cyano, hydroxyl, carboxyl or an ester thereof (e.g., a lower alkyl ester), aminocarbonyl, acyl (e.g., a lower alkanoyl), alkoxy of 1 to 4 carbon atoms, etc.

Examples of the aralkyl group include alkyl groups of 1 to 4 carbon atoms substituted with an aryl group represented by phenyl, thienyl, pyridyl, naphthyl, etc. (e.g., benzyl, phenethyl, furfuryl, phenylpropyl, phenylbutyl, etc.). These groups may have a substituent on the aromatic ring such as a halogen (e.g., fluorine, chlorine, iodine, bromine), nitro, cyano, hydroxyl, carboxyl or an ester thereof (e.g., a lower alkyl ester), aminocarbonyl, acyl (e.g., a lower alkanoyl), alkoxy of 1 to 4 carbon atoms, alkyl of 1 to 4 carbon atoms, etc.

Examples of the aryl group of 1 to 24 carbon atoms include carbocyclic aromatic compounds and heterocyclic aromatic compounds such as phenyl, furyl, thienyl, pyridyl, naphthyl group, etc.; these groups may have a substituent such as a halogen (e.g., fluorine, chlorine, bromine), an alkyl group of 1 to 4 carbon atoms and an alkoxy group of 1 to 4 carbon atoms.

Examples of the acyl group of 1 to 18 carbon atoms for $R_1$, $R_2$ and $R_3$ include formyl, acetyl, propionyl, butyryl, isobutyryl, valeryl, isovaleryl, pivaloyl, hexanoyl, heptanoyl, octanoyl, nonanoyl, decanoyl, lauroyl, myristoyl, palmitoyl, stearoyl, benzoyl, etc. Among the above examples, the acyl group of 1 to 7 carbon atoms is preferably used.

The substituents for $R_1$, $R_2$ and $R_3$ described above include protective groups, which are often used in ordinary chemical reactions.

Examples of the protective groups include benzyl groups which may have substituent(s), acyl groups, alkoxyalkyl groups, etc.

Examples of the benzyl groups which may have substituent(s) include benzyl, p-methoxybenzyl, o-nitrobenzyl, p-nitrobenzyl, p-chlorobenzyl, p-bromobenzyl, p-cyanobenzyl, etc. These groups are also included in the aralkyl groups mentioned above.

Examples of the alkoxyalkyl groups include methoxymethyl, tert-butoxymethyl, 1-ethoxyethyl, 1-methyl-1-methoxyethyl, etc. These groups are also inclued in the alkyl group mentioned above.

Examples of the acyl groups are the same examples previously indicated.

The compounds represented by the formula

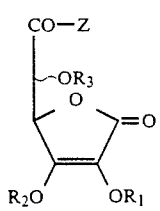

(II')

[wherein Z represents

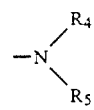

or $-SR_6$, $R_4$ and $R_5$ independently represent a hydrogen or a hydrocarbon group of 1 to 24 carbon atoms, or $R_4$ and $R_5$ may together form $-(CH_2)_n$ in which n is an integer of 4 to 7, $R_6$ represents a hydrocarbon group of 1 to 24 carbon atoms, $R_1$ and $R_2$ independently represent a hydrogen or a protective group, at least one of $R_1$ and $R_2$ is a protective group, $R_3$ represents a hydrogen, or an acyl group of 1 to 18 carbon atoms, and $\sim$ represents the R-configuration or the S-configuration.] are not only novel compounds but also are useful intermediates for production of the compounds represented by the formula

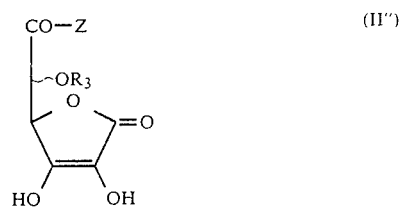

(II'')

[wherein Z represents

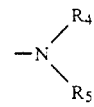

or $-SR_6$, $R_4$ and $R_5$ independently represent a hydrogen or a hydrocarbon group of 1 to 24 carbon atoms, or $R_4$ and $R_5$ may together form $-CH_2-_n$ is an integer of 4 to 7, $R_6$ represents a hydrocarbon group of 1 to 24 carbon atoms, $R_3$ represents a hydrogen or an acyl group of 1 to 18 carbon atoms, and $\sim$ represents the R-configuration or the S-configuration.].

In the above formula (II), it is preferable that both of $R_1$ and $R_2$ represent a protective group. The protective group is preferably a benzyl group mentioned before.

In the compounds represented by the formula (II') and (II''), a hydrocarbon group of 1 to 24 carbon atoms, a protective group and an acyl group have the same definition as previously indicated.

This point is described in the following reaction schemes 1 to 5. The compounds represented by both of the above formulas (II') and (II'') are included in the scope of the compounds (II) of the present invention.

The compounds (II) of the present invention are produced by the use of saccharoascorbic acid (I) as the starting material.

When Z of the formula (II) is

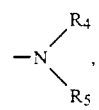

the production method for the compounds (II) of the present invention comprises an amidation synthetic reaction of saccharoascorbic acid.

For example, the production is carried out by the method comprising the amidation synthetic reaction of 2- and 3-hydroxyl-substituted saccharoascorbic acid. The method preferably comprises the amidation synthetic reaction of 2-, 3- and 5-hydroxyl-substituted saccharoascorbic acid.

These methods are hereinafter described in detail.

Scheme 1

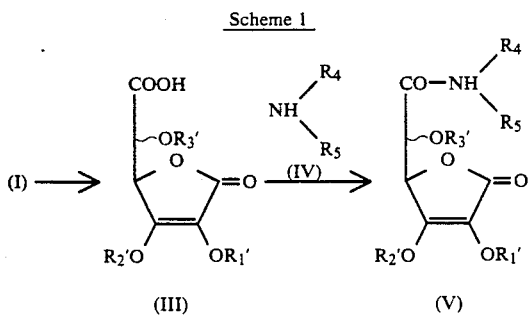

[wherein $R_4$ and $R_5$ have the same definition as before, $R_1'$, $R_2'$ and $R_3'$ independently represent hydrogen, an acyl of 1 to 18 carbon atoms or a hydrocarbon group of 1 to 24 carbon atoms; at least one of $R_1'$, $R_2'$ and $R_3'$ being other than a hydrogen.]

As shown in scheme 1, a compound represented by the formula (V) is obtained by the reaction of the compound (III) with an ammonia or an amine represented by formula (IV).

The compound (IV) is an ammonia, a primary amine or secondary amine, represented by the formula (IV).

Production of the compound (III) can be achieved by a known method for protection of a hydroxyl group (European Patent Laid-open No. 0,295,842). In general, the 2- and 3-hydroxyl groups are substituted by a benzyl group identified above, and the 5-hydroxyl group is substituted by an acyl group identified above. In another case, for example, where $R_1'$ and $R_2'$ independently represent hydrogen, an acyl group or another hydrocarbon group, the production of the compound (III) can be carried out according to the scheme 4 or 5 described after. This production can be preferably carried out by acylation of free hydroxyl group in the compound (III-1)~(III-3) described after.

Production of the compound (V) by reaction of the compound (III) with (IV) can be also achieved by a known method of amidation synthetic reaction.

For example, the reaction can be carried out using a lithium carbonate, sodium hydrogen carbonate, potassium hydrogen carbonate, lithium hydrogen carbonate, calcium hydroxide, barium hydroxide, ammonia and primary, secondary and tertiary amines.

Any reaction solvent can be used without particular limitation, as long as it does not interfere with the reaction, but water and highly hydrophilic solvents are normally used, such as acetone, methyl ethyl ketone, methanol, ethanol, n-propanol, isopropanol, acetonitrile, propionitrile, tert-butanol, dioxane, tetrahydrofuran, ethyl ether, ethylene glycol dimethyl ether, diethylene glycol dimethyl ether, ethyl acetate, dimethylformamide, dimethlacetamide, dimethylsulfoxide and hexamethylphosphoramide. These solvents may be used in combination.

Reaction temperature ranges from $-10°$ to $120°$ C.; reaction time ranges from about 1 to 20 hours.

Removal of the benzyl group can normally be achieved by the catalytic hydrogenation.

Examples of the catalyst include palladium, palladium chloride, platinum oxide, platinum black, ruthenium, etc. These may be supported on activated carbon, alumina, silica gel, etc.

Any reaction solvent can be used without particular limitation, as long as it does not interfere with the reaction. Examples of the solvents include methanol, ethanol, propanol, ethyl acetate, acetic acid, acetonitrile, dioxane, tetrahydrofuran, ethyl ether, 1,2-dimethoxyethane, ethylene glycol dimethyl ether, chloroform, dichloromethane, benzene, toluene, water, etc. These solvents can be used singly or in combination.

Reaction temperature ranges from $10°$ to $100°$ C. Reaction time is from 1 to 10 hours. The reaction can be carried out under atmospheric pressure or higher pressure.

As described above, the compounds in which $R_1'$, $R_2'$ and/or $R_3'$, which is a protective group, is removed from the compounds (V) are also included in the scope of the compounds (II) of the present invention. The compounds (V), of course, are included in the scope of the compounds (II) of the present invention.

When Z of the formula (II) is

the other production method for the compound (II) of the present invention is described in scheme 2.

Scheme 2

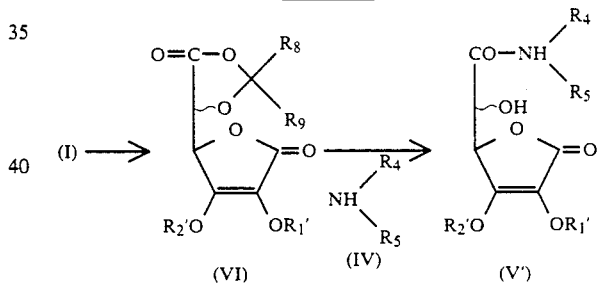

[wherein $R_8$ and $R_9$ independently represent hydrogen, methyl, ethyl, phenyl or $R_8$ and $R_9$ are bonded to form $-(CH_2)_{4-5}$; $R_1'$ and $R_2'$ have the same definition as before; and $R_4$ and $R_5$ also have the same definition as before.]

As shown in scheme 2, a compound (V') is obtained by reaction of a compound (VI) with a compound (IV). When either of $R_1'$ and $R_2'$ represents a group that can be removed by reduction or by hydrolysis, the said group may optionaly be removed by the method described as before. The compound (VI) can be obtained by a known method (European Patent Laid-open No. 0,295,842).

Both the compounds (V') and the compounds in which $R_1'$ and/or $R_2'$ is or are removed from the compounds (V') are included in the scope of the compounds (II) of the present invention.

The reaction of a compound (VI) with a compound (IV) can be carried out by heating the reaction mixture in an organic solvent.

Examples of the solvent include hydrocarbon compounds (e.g., hexane, benzene, toluene, etc.), halogenated hydrocarbon compounds (e.g., chloroform, dichloromethane, 1,2,-dichloroethane, etc.), ethers (diethyl ether, tetrahydrofuran, dioxane, etc.), acetonitrile, dimethylformamide, dimethylsulfoxide, etc.

Reaction temperature ranges from 50° to 150° C. Reaction time is from 5 to 20 hours.

When Z of the formula (II) is —SR$_6$, the production method for the compounds (II) of the present invention comprises subjecting saccharoascorbic acid to thiolesterification.

The method is hereinafter described in detail.

Scheme 3

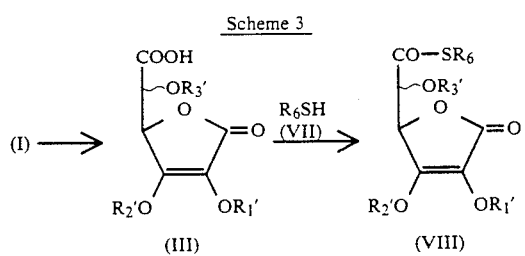

[wherein R$_6$ has the same definition as before; R$_1'$, R$_2'$ and R$_3'$ also have the same definition as before; and at least one of R$_1'$, R$_2'$ and R$_3'$ being other than hydrogen.]

As shown in scheme 3, a compound represented by the formula (VIII) is obtained by the reaction of a compound (III) with a thiol represented by the formula (VII).

Production of the compounds (III) is the same as before.

Synthesis of the compounds (VIII) by reaction of a compound (III) with (VII) can be also achieved by a known method of thiol esterification.

For example, the reaction can be carried out using the same carboxyl-activating reagent as mentioned before. The organic solvent mentioned before can be also used.

The compound (III) may be converted to an acid halide using the halogenating agent mentioned before.

Reaction temperature for this reaction ranges from −10° to 120° C. Reaction time is about 1 to 5 hours.

When at least one of R$_1'$, R$_2'$ and R$_3'$ in the compound (VI) is a group that can be removed, such as an acyl group, a benzyl group described before, etc., the group may optionally be removed.

Removal of the acyl group can be achieved by the same manner mentioned before.

Removal of the benzyl group can normally be acheived by a reaction with a Lewis acid.

Examples of the Lewis acid include aluminum chloride, titanium tetrachloride, tin tetrachloride, boron trifluoride ether complex, boron tribromide, zinc chloride, etc.

Any reaction solvent can be used without particular limitation, as long as it does not interfere with the reaction. Examples of the solvents include hydrocarbons (e.g., chloroform, dichloromethane, 1,2-dichloroethane, etc.), ethers (e.g., diethyl ether, tetrahydrofuran, dioxane, etc.), acetonitrile, etc.

Reaction temperature ranges from −10° to 120° C. Reaction time is from about 5 hours to 2 days.

Both the compounds (VIII) and the compounds in which R$_1'$, R$_2'$ and/or R$_3'$ is removed from the compounds (VIII) are included in the scope of the compounds (II) of the present invention.

When Z of the formula (II) is —OR$_7$, the production method for the compounds (II) of the present invention is hereinafter described in detail.

Scheme 4

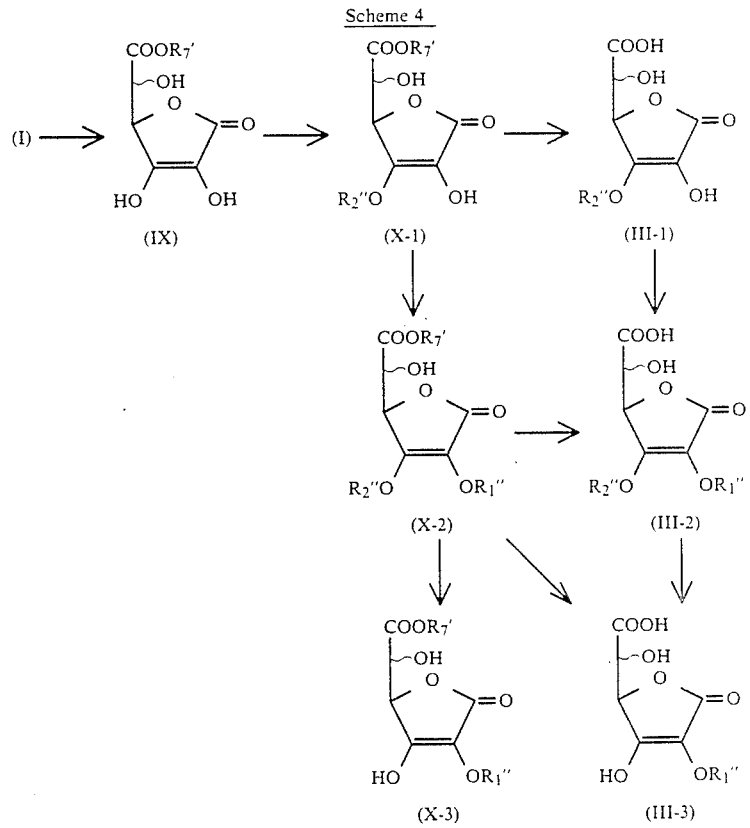

[wherein $R_7'$ represents a hydrocarbon group of 1 to 24 carbon atoms, and $R_1''$ and $R_2''$ also represent a hydrocarbon group of 1 to 24 carbon atoms.]

The compound (IX) is obtained by a known method (European Patent Laid-Open No. 0,295,842). And further, the compounds (X-1)~(X-3) and (III-1)~(III-3) can be produced from the compounds (IX) as a starting material.

The compounds (X-1) are produced by the reaction of a compound (IX) with a compound represented by the formula $$R_2''X$$

[wherein $R_2''$ has the same definition as before; X represents a halogen such as chlorine, bromine, iodine, etc., an alkylsulfonyloxy such as methanesulfonyloxy, trifluoromethanesulfonyloxy, etc., an arylsulfonyloxy such as benzenesulfonyloxy, p-toluenesulfonyloxy, etc.] in the presence of an equivalent amount of a base.

Further, the compounds (X-1) are hydrolyzed by a conventional method to obtain the compounds (III-1). When $R_7'$ of the compounds (X-1) is a group that can removed by reduction, a compound (III-1) can be also obtained by reduction.

The compounds (X-2) are produced by the reaction of a compound (X-1) with a compound represented by the formula $$R_1''X$$

[wherein $R_1''$ and X have the same definition as before; and $R_1''$ is not the same as $R_2''$.] in the presence of an equivalent amount of a base.

Further, the compounds (X-2) are hydrolyzed by a conventional method to obtain a compound (III-2). When $R_7'$ of a compound (X-2) is removed by reduction, a compound (III-2) can be also obtained by reduction.

When $R_2''$ of a compound (X-2) at the 3-position is removed by reduction, a compound (X-3) can be produced from a compound (X-2) as a starting material. And also a compound (III-3) can be produced from a compound (III-2) as a starting material.

Specially in the case where both of $R_2''$ and $R_7'$ are groups that can be removed by reduction or by hydrolysis, a compound (III-3) can be produced from a compound (X-2) by reduction or by hydrolysis in one step.

Examples of the groups that can be removed by reduction include benzyl, p-methoxybenzyl, o-nitrobenzyl, p-nitrobenzyl. p-chlorobenzyl, p-bromobenzyl, p-cyanobenzyl, diphenylmethyl, etc.

Examples of the groups that can be removed by hydrolysis include an alkoxyalkyl group such as methoxymethyl, tert-butoxymethyl, 1-ethoxyethyl, 1-methyl-1-methoxyethyl, etc. and so on.

The etherifications mentioned above are normally carried out under following conditions;

A base can be used for this reaction without particular limitation. Examples of such bases include sodium hydride, calcium hydride, lithium hydride, lithium hydroxide, lithium hydrogen carbonate, lithium carbonate, sodium methoxide, sodium ethoxide, sodium hydroxide sodium hydrogen carbonate, sodium carbonate, potassium hydroxide, potassium hydrogen carbonate, potassium carbonate, magnesium hydroxide, magnesium carbonate, calcium hydroxide, barium hydroxide, barium carbonate, pyridine, tertiary amines, ammonium hydroxide having substitutents (N+OH−), etc.

A reaction solvent can be used without particular limitation, as long as it does not interfere with the reaction, but normally polar solvent is used. Examples include acetonitrile, propionitrile, benzonitrile, formamide, dimethyl formamide, dimethyl acetamide, dimethylsulfoxide, sulfolane, hexamethylphosphoramide, acetone, methylethylketone, dioxane, tetrahydrofuran, ethylene glycol dimethyl ether, diethylene glycol dimethyl ether, water, etc. These solvents can be used singly or in combination.

Reaction temperature ranges from 0° to 100° C., preferably 10° to 80° C.

Reaction time depends upon reactants, reaction reagents, reaction conditions, etc. It normally ranges from 30 minutes to 4 days.

The hydrolysis of an ester at the 6-position and $-OR_2'$ at the 3-position can be normally carried out under acidic conditions.

Any acid can be used without particular limitation.

Examples of acids include hydrogen chloride, hydrogen bromide, hydrogen iodide, hydrogen fluoride, sulfuric acid, fluorosulfuric acid, perchloric acid, phosphoric acid, boric acid, p-toluenesulfonic acid, trifluoromethanesulfonic acid, methanesulfonic acid, trifluoroacetic acid, trichloroacetic acid, acetic acid, H+ type ion-exchange resin, etc. These substances may be used as they are, or dissolved or suspended in water or organic solvent as necessary. These acids can be used singly or in combination.

A reaction solvent can be used without particular limitation, as long as it does not interfere with the reaction. Preferably hydrophilic solvent is normally used. Examples of the solvent include acetone, methylethylketone, methanol, ethanol, n-propanol, iso-propanol, acetonitrile, propionitrile, tert-butanol, dioxane, tetrahydrofuran, ethylether, ethylene glycol dimethyl ether, diethylene glycol dimethyl ether, ethyl acetate, dimethylformamide, dimethylacetamide, dimethylsulfoxide, hexamethylphosphoramide, water, etc. These solvents can be used singly or in combination.

Reaction temperature ranges from 0° to 100° C., preferably 10° to 80° C.

Reaction time depends upon reactants, reaction reagents, reaction conditions, etc. It normally ranges from 1 to 10 hours.

The reduction can be normally carried out by catalytic hydrogenation.

Examples of the catalyst include palladium, palladium chloride, platinum oxide, platinum black, ruthenium, etc. These may be supported on activated carbon, alumina, silica gel, etc.

A reaction solvent can be used without limitation. Examples of the solvents include methanol, ethanol, propanol, ethyl acetate, acetic acid, acetonitrile, dioxane, tetrahydrofuran, ethyl ether, 1,2-dimethoxyethane, ethylene glycol dimethyl ether, chloroform, dichloromethane, benzene, toluene, water and so on. These solvents can be used singly or in combination.

Reaction temperature ranges from 10° to 100° C. Reaction time is 1 to 10 hours. The reaction can be carried out under atomospheric pressure or higher pressure.

The other production method is shown in scheme 5 as follows;

Scheme 5

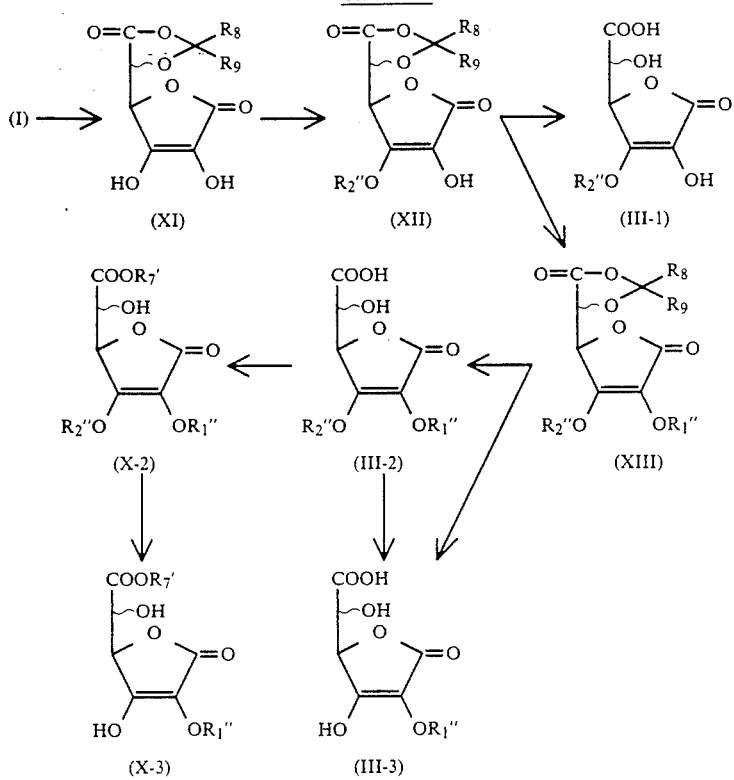

[wherein $R_8$ and $R_9$ have the same definition as before, and $R_1''$, $R_2''$ and $R_7'$ have the same definition as before.]

As shown in scheme 5, the compounds (X-2)~(X-3) and (III-1)~(III-3) are produced from the compounds (XII). A compound (XI), which forms 4-oxo-1,3-dioxorane ring to protect at 5- and 6-position, can be obtained by a known method (European Patent Laid-open No. 0,295,842).

The compounds (XII) are produced by the reaction of a compound represented by the formula $$R_2''X$$

[wherein $R_2''$ and X have the same definition as before.] with a compound (XI) in the presence of an equivalent amount of a base. The 4-oxo-1,3-dioxorane ring of a compound (XII) is subjected to hydrolysis to obtain a compound (III-1).

The compounds (XIII) are produced by the reaction of a compound represented by the formula $$R_1''X$$

[wherein $R_1''$ and X have the same definition as before.] with a compound (XII) in the presence of an equivalent amount of a base. $R_1''$ and $R_2''$ are different from each other.

The compounds (XIII) are subjected to hydrolysis to obtain a compound (III-2). The 6-carboxylic group of the obtained compound (III-2) is subjected to esterification to obtain a compound (X-2).

Specially in the case that $R_2'$ of the compounds (III-2) or (X-2) can be removed by reduction, the compounds (III-3) and (X-3) are respectively produced from the compounds (III-2) and (X-2) by a conventional method.

These production processes have been described as before.

In case that $R_2'$ of the compounds (XIII) is removed by hydrolysis, a compound (III-3) can be obtained by hydrolyzing a compound (XIII) in one step.

The process proceeding from the compound (I) to (XI) is carried out by reaction of a compound (I) with a ketone or aldehyde such as formaldehyde, acetaldehyde, acetone, propionaldehyde, methylethylketone, diethylketone, cyclopentanone, cyclohexanone, benzaldehyde, etc. in the presence of an acidic catalyst. And also, the compounds (XI) can be obtained by reacting a compound (I) with a ketal or an acetal, which is respectively produced from the said ketone or aldehyde with a lower alkanol.

A reaction solvent can be used without particular limitation, as long as it does not interfere with the reaction. Examples of the solvent include acetonitrile, propionitrile, benzonitrile, nitromethane, nitroethane, nitrobenzene, dichloromethane, chloroform, tetrachloromethane, 1,1-dichloroethane, 1,2-dichloroethane, hexane, cyclohexane, benzene, toluene, xylene, dioxane, tetrahydrofuran, 1,2-dimethoxyethane, ethylene glycol dimethyl ether, diethyl carbonate, dimethylformamide, dimethylsulfoxide, etc. The said ketone, the said aldehyde, the said ketal and the said acetal can be used as a solvent. These solvents can be used singly or in combination.

Examples of acidic catalysts include a mineral acid such as hydrogen chloride, hydrogen bromide, hydrogen iodide, hydrogen fluoride, perchloric acid, sulfuric acid, fluorosulfuric acid, phosphoric acid, boric acid, etc., an organic acid such as p-toluenesulfonic acid, benzenesulfonic acid, methanesulfonic acid, trifluoromethanesulfonic acid, trifluoroacetic acid, H+ type ion-exchange resin, etc., Lewis acids such as boron trifluoride, boron trichloride, boron tribromide, boron triiodide, aluminum chloride, titanium tetrachloride, zinc chloride, stannous chloride, stannic chloride, etc.

Reaction temperature ranges from 0° to 100° C. Reaction time is from 1 to 24 hours.

In the etherification, the hydrolysis and the reduction, the same reaction conditions as before can be used.

The process proceeding from the compound (III-2) to (X-2) can be carried out by a conventional esterification.

For example,

① Direct esterification: reacting a compound (III-2) with an alcohol represented by the formula

R₇'OH

[wherein R₇' has the same definition as before.] in the presence of an acidic catalyst.

② reacting a compound (III-2) with a compound represented by the formula

R₇'X

[wherein R₇' and X have the same definition as before.] in the presence of a base.

③ reacting a compound (III-2) with an alcohol represented by the formula

R₇'OH

[wherein R₇' has the same definition as before.] in the presence of a condensation reagent such as dicyclohexylcarbodiimide, etc.

④ reacting a compound (III-2) with an olefinic compound such as isobutylene, etc. in the presence of an acidic catalyst.

⑤ reacting a compound (III-2) with an O-alkylating agent such as diazomethane, orthoformate, etc.

All of the compounds (III-1)~(III-3) and (X-1)~(X-3) described in the schemes 4 and 5 are included in the scope of the compound (II) of the present invention.

The derivatives of saccharoascorbic acid produced by the production method of the present invention can easily be isolated by routine means such as extraction, chromatography (e.g., silica gel, polystyrene resin, activated charcol, reverse phase, normal phase chromatography) or recrystallization from the residue obtained after distillation of low boiling point substances such as the solvent from the reaction product.

Also, the derivatives, which have at least one hydroxyl group at the 2- or 3-position, or the 6-carboxyl group, can be converted to their salts by reaction with an appropriate base such as an alkali metal oxide, alkali metal hydroxide, alkali metal carbonate or bicarbonate, alkaline earth metal oxide, alkaline earth metal hydroxide, alkaline earth metal carbonate or an amine, or and ammonium hydroxide, or by contact with a cation exchange resin substituted with an appropriate alkali metal, alkaline earth metal, or an appropriate ammonium ion. It is also possible to isolate the desired derivatives in the form of a salt using routine means such as recrystallization and reprecipitation after direct conversion of the derivatives to their salt without isolating the derivatives by neutralizing the reaction mixture by the addition of an appropriate base such as an alkali metal oxide, alkali metal hydroxide, alkali metal carbonate or bicarbonate, alkaline earth metal oxide, alkaline earth metal hydroxide or alkaline earth metal carbonate, or an amine, or an ammonium hydroxide, or by bringing the reaction mixture into contact with a cation exchange resin substituted with an appropriate alkali metal, alkaline earth metal or an ammonium ion, and then, distilling off the solvent.

Examples of salts of the derivatives include salts of alkali metals (e.g., lithium, sodium, potassium, etc), salts of alkaline earth metals (e.g., magnesium, calcium, barium, etc), ammonium salts, pyridinium salts and substituted ammonium salts. Examples of substituted ammonium salts include methylammonium, ethylammonium, propylammonium, butylammonium, pentylammonium, hexylammonium, anilinium, benzylammonium, dimethylammonium, diethylammonium, dipropylammonium, dibutylammonium, dipenttylammonium, dihexylammonium, dianilinium, piperidinium, morpholinium, pyridazinium, pyrrolidinium, dibenzylammonium, trimethylammonium, triethylammonium, tripropylammonium, tributylammonium, tripentylammonium, trihexylammonium, tribenzylammonium tetramethylammonium, tertaethylammonium, tetrapropylammonium, tetrabutylammonium, tetrapentylammonium, tetrahexylammonium, trimethylphenylammonium, trimethylbenzylammonium, triethylphenylammonium, triethylbenzylammonium, tripropylphenylammonium, tripropylbenzylammonium, tributylphenylammonium and tributylbenzylammonium.

The compounds mentioned above are novel and very useful. For example, dichiral compounds, which are intermediates for producing liquid crystal compounds, can be obtained using a compounds of the present invention as a starting material. This process are shown as follows;

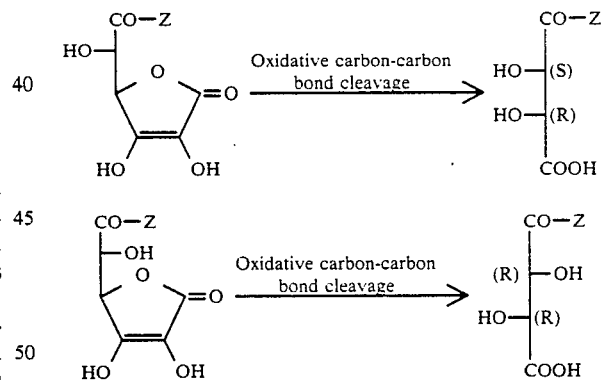

From the example shown above, it is clear that the dichiral compounds can be easily obtained from the compounds of the present invention. The dichiral compounds can be used according to the disclosure of European Patent Laid-open No. 0,322,862 to obtain a liquid crystal compound.

In case where a hydroxyl group at the 2- and/or 3-position is substituted, dichiral compounds can be obtained by the same manner shown in the above scheme.

EXAMPLES

The compounds of the present invention are hereinafter described in more detail by means of the following examples.

EXAMPLE 1

(5,6-0-isopropylidene-D-glucosaccharoascorbic acid)

Three drops of concentrated sulfuric acid was added to a mixture of 15.0 g of D-glucosaccharoascorbic acid, 20.55 g of 2,2-dimethoxypropane and 150 ml of acetone, followed by stirring at room temperature for 4 hours. Then, a small amount of pyridine (about 10 drops) was added and the mixture was evaporated under reduced pressure. The residue was subjected to silica gel column chromatography (solvent: ethyl acetate). The resulting solid was recrystallized from acetone-dichloromethane (1:10) to yield 16.1 g of 5,6-0-isopropylidene-D-glucosaccharoascorbic acid.

Yield: 88.7%, Melting point: 162°–163° C.

IR (KBr) cm$^{-1}$, 3300, 3200, 1775, 1750, 1700, 1670.

$^1$H-NMR (DMSO-d$_6$) δ. 1.58(s, 6H), 4.97(s, 2H). Figuring for OH group is difficult because its band is very broad. Elemental analysis (%). Calculated for C$_9$H$_{10}$O$_7$: C 46.96; H 4.38. Found: C 46.84; H 4.32.

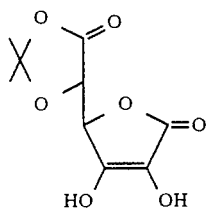

EXAMPLE 2

(5,6-0-isopropylidene-L-gulosaccharoascorbic acid)

One drop of concentrated sulfuric acid was added to a mixture of 0.40 g of L-gulosaccharoascorbic acid, 1.09 g of 2,2-dimethoxypropane and 10 ml of acetone, followed by stirring at room temperature for 3 hours. Then, four drops of pyridine was added and the mixture was evaporated under reduced pressure. The residue was subjected to silica gel column chromatography (solvent: ethyl acetate). The resulting product was recrystallized from ethyl acetate-dichloromethane=1:10 to yield 0.231 g of 5,6-0-isopropylidene-L-gulosaccharoascorbic acid.

Yield: 47.7%. Melting point: 158°–159° C.

IR (KBr) cm$^{-1}$. 3500–3100, 1765, 1705.

$^1$H-NMR (DMSO-d$_6$) δ. 1.47(s, 3H), 1.55(s, 3H), 4.95(m, 2H). Figuring for OH group is difficult because its band is very broad. Elemental analysis (%). Calculated for C$_9$H$_{10}$O$_7$: C 46.96; H 4.38. Found: C 46.42; H 4.33.

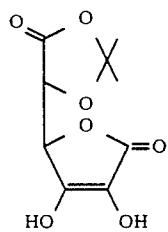

EXAMPLE 3

(5,6-0-cyclohexylidene-D-glucosaccharoascorbic acid)

A mixture comprising 3.0 g of D-glucosaccharoascorbic acid, 60 ml of cyclohexanonedimethylacetal and three drops of concentrated sulfuric acid was stirred at room temperature overnight. The mixture was evaporated under reduced pressure; the residue was subjected to silica gel column chromatography (solvent: dichloromethane-ethyl acetate). The resulting product was recrystallized from dichloromethane-n-hexane to yield 1.53 g of 5,6-0-cyclohexylidene-D-glucosaccharoascorbic acid.0.5 hydrate.

Yield: 34.7%. Melting point: 80°–85° C.

IR (KBr) cm$^{-1}$. 3500–3100, 1770, 1690.

$^1$H-NMR (DMSO-d$_6$) δ. 1.20–2.00(m, 10H), 5.06(s, 2H), Ca. 8.5(br. 1H), Ca. 11.1(br. 1H). Elemental analysis (%). Calculated for C$_{12}$H$_{14}$O$_7$.0.5H$_2$O: C 51.61; H 5.41. Found: C 51.48; H 5.18.

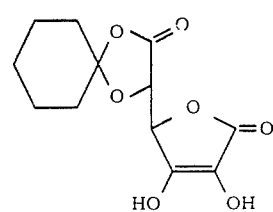

EXAMPLE 4

(5,6-0-isopropylidene-3-0-methyl-D-glucosaccharoascorbic acid)

2.00 g of 5,6-0-isopropylidene-D-glucosaccharoascorbic acid produced in accordance with Example 1 was dissolved in 20 ml of dimethylsulfoxide. To this solution was added 0.66 g of potassium carbonate, followed by dropwise addition of 1.36 g of methyl iodide and stirring at room temperature for 30 minutes. Then, the remaining insoluble salt was removed by filtration. The filtrate was diluted with 200 ml of water and extracted with dichloromethane four times. The extract was washed with water (4 times), dried and evaporated under reduced pressure. The residue was subjected to silica gel column chromatography (solvent: ethyl acetate-hexane=1:1). The resulting product was recrystallized from dichloromethane-n-hexane=1:5 to yield 1.09 g of 5,6-0-isopropylidene-3-0-methyl-D-glucosaccharoascorbic acid.

Yield: 51.3%. Melting point: 98°–99° C.

IR (KBr) cm$^{-1}$. 3550, 3400–3100, 1800–1760, 1705.

$^1$H-NMR (CDCl$_3$) δ. 1.57(s, 3H), 1.63(s, 3H), 4.18(s, 3H), 4.80(d, 1H, J=2 Hz), 4.97(d, 1H, J=2 Hz), 5.27(br, OH). M.S m/e 244(M), 229.

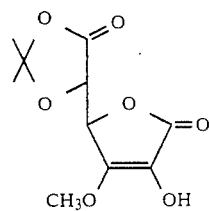

EXAMPLE 5

(5,6-0-isopropylidene-3-0-methoxymethyl-D-glucosaccharoascorbic acid)

2.00 g of 5,6-0-isopropylidene-D-glucosaccharoascorbic acid produced in accordance with Example 1 was dissolved in 20 ml of dimethylsulfoxide. To this solution was added 1.20 g of potassium carbonate, followed by dropwise addition of 0.95 g of chloromethyl methyl ether and stirring at room temperature for 30 minutes. Then, the remaining insoluble salt was removed by filtration. The filtrate was diluted with 200 ml of water and thrice extracted with dichloromethane. The extract was washed with water (4 times), dried and evaporated under reduced pressure. The residue was subjected to silica gel column chromatography (solvent: ethyl acetate-hexane=1:1). The resulting product was recrystallized from ether-hexane=1:5 to yield 1.31 g of 5,6-0-isopropylidene-3-0-methoxymethyl-D-glucosaccharoascorbic acid.

Yield: 55.0%. Melting point: 93°-95° C.

IR (KBr) cm$^{-1}$. 3400-3150, 1770, 1700.

$^1$H-NMR (CDCl$_3$) δ. 1.58(s, 3H), 1.65(s, 3H), 3.62(s, 3H), 4.82(d, 1H, J=2 Hz), 5.03(d, 1H, J=2 Hz), 5.28(d, 1H, J=6 Hz), 5.36(d, 1H, J=6 Hz), 5.6-6.8(br, OH). M.S m/e 274(M), 259, 244. Elemental analysis (%). Calculated for C$_{11}$H$_{14}$O$_8$: C 48.18; H 5.15. Found: C 48.31; H 5.13.

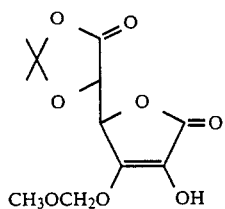

EXAMPLE 6

(5,6-isopropylidene-3-0-methoxymethyl-2-0-methyl-D-glucosaccharoascorbic acid)

0.93 g of 5,6-0-isopropylidene-3-0-methoxymethyl-D-glucosaccharoascorbic acid produced in accordance with Example 5 was dissolved in 10 ml of dimethylsulfoxide. To this solution was added 0.49 g of potassium carbonate, followed by dropwise addition of 0.72 g of methyl iodide and stirring at room temperature for 1 hour. Then, the remaining insoluble salt was removed by filtration. The filtrate was diluted with 100 ml of water and thrice extracted with dichloromethane. The extract was washed (4 times), dried and evaporated under reduced pressure. The residue was subjected to silica gel column chromatography (solvent: ethyl acetate-hexane=1:1). The resulting product was recrystallized from dichloromethane-hexane=1:3 to yield 0.68 g of 5,6-0-isopropylidene-3-0-methoxymethyl-2-0-methyl-D-glucosaccharoascorbic acid.

Yield: 69.6%. Melting point: 104°-105.5° C.

IR (KBr) cm$^{-1}$. 1780, 1765, 1685.

$^1$H-NMR (CDCl$_3$) δ. 1.58(s, 3H), 1.65(s, 3H), 3.53(s, 3H), 3.87(s, 3H), 4.81(d, 1H, J=2 Hz), 4.97(d, 1H, J=2 Hz), 5.38(d, 1H, J=6 Hz), 5.49(d, 1H, J=6 Hz). M.S m/e 288(M), 273, 258.

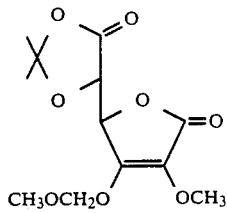

EXAMPLE 7

(5,6-0-isopropylidene-3-0-octadecyl-D-glucosaccharoascorbic acid)

10.0 g of 5,6-0-isopropylidene-D-glucosaccharoascorbic acid produced in accordance with Example 1 was dissolved in 40 ml of dimethylformamide. To this solution were added 3.60 g of potassium carbonate and then 16.5 g of n-octadecyl iodide, followed by stirring at 80° C. for 6 hours. Then, the reaction mixture was diluted with 200 ml of water and twice extracted with ethyl ether. The extract was washed (2 times), dried and evaporated under reduced pressure. The residue was subjected to silica gel column chromatography (solvent: ethyl acetate-hexane=1:1) to yield 4.70 g of 5,6-0-isopropylidene-3-0-octadecyl-D-glucosaccharoascorbic acid.

Yield: 22.4%. This product was used for the next reaction without recrystallization.

IR (KBr) cm$^{-1}$. 3400-3250, 1800, 1770, 1710.

$^1$H-NMR (CDCl$_3$) δ. 0.88(t, 3H), 1.20-1.85(m, 32H), 1.57(s, 3H), 1.63(s, 3H), 4.47(t, 2H, J=7 Hz), 4.79(d, 1H, J=2 Hz), 4.96(d, 1H, J=2 Hz), 5.25(br, OH). M.S m/e 482(M), 467.

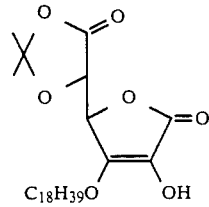

EXAMPLE 8

(3-0-benzyl-5,6-isopropylidene-D-glucosaccharoascorbic acid)

2.00 g of 5,6-0-isopropylidene-D-glucosaccharoascorbic acid produced in accordance with Example 1 was dissolved in 15 ml of dimethylsulfoxide. To this solution were added 1.20 g of potassium carbonate, followed by dropwise addition of 1.49 g of benzyl bromide and stirring at room temperature for 1 hour. Then, the remaining insoluble salt was removed by filtration; the filtrate was diluted with 200 ml of water and thrice extracted with dichloromethane. The extract was washed with water (4 times), dried and evaporated under reduced pressure. The residue was subjected to silica gel column chromatography (solvent: ethyl acetate-hexane=1:1) to yield 1.67 g of pasty 3-0-benzyl-5,6-0-isopropylidene-D-glucosaccharoascorbic acid.

Yield: 59.9%. This product was partially crystallized in ether-hexane=1:4 to yield 0.55 g of a crystal. Melting point: 137°-139° C.

IR (KBr) cm$^{-1}$. 3430, 1805, 1770, 1705.

¹H-NMR (CDCl₃) δ. 1.55(s, 6H), 4.81(d, 1H, J=2 Hz), 5.00(d, 1H, J=2 Hz), 5.40(br, OH), 5.51(s, 2H), 7.38(s, 5H). M.S m/e 320(M+).

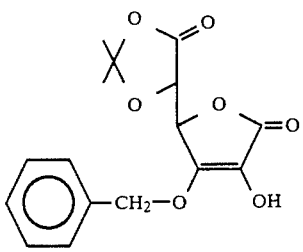

EXAMPLE 9

(3-0-benzyl-5,6-0-isopropylidene-2-0-octadecyl-D-glucosaccharoascorbic acid)

11.19 g of 3-0-benzyl-5,6-0-isopropylidene-D-glucosaccharoascorbic acid produced in accordance with Example 8 was dissolved in 60 ml of dimethylsulfoxide. To this solution were added 4.83 g of potassium carbonate and then a solution of 13.29 g of n-octadecyl iodide in 60 ml of tetrahydrofuran, followed by stirring at room temperature for 3 days. Then, the reaction mixture was diluted with 500 ml of water and thrice extracted with ethyl ether. The extract was washed with water (2 times), dried and evaporated under reduced pressure. The residue was subjected to silica gel column chromatography (solvent: ethyl acetate-hexane=1:5) to yield 11.56 g of 3-0-benzyl-5,6-0-isopropylidene-2-0-octadecyl-D-glucosaccharoascorbic acid.

Yield: 57.8%.

IR (KBr) cm⁻¹. 1795, 1770, 1680.

¹H-NMR (CDCl₃) δ. 0.88(t, 3H), 1.15-1.73(m, 32H), 1.55(s, 3H), 1.58(s, 3H), 4.08(t, 2H, J=7 Hz), 4.78(d, 1H, J=1Hz), 4.96(d, 1H, J=2 Hz), 5.47(s, 1H), 5.49(s, 1H), 7.37(s, 5H). M.S m/e 572(M), 557, 480.

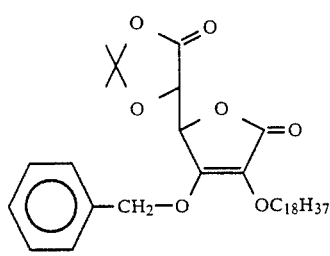

EXAMPLE 10

(Methyl ester of 3-0-octadecyl-D-glucosaccharoascorbic acid)

4.22 g of methyl ester.monohydrate of D-glucosaccharoascorbic acid was dissolved in 20 ml of dimethylsulfoxide. To this solution were added 2.49 g of potassium carbonate and then a solution of 7.23 g of n-octadecyl iodide in 20 ml of tetrahydrofuran, followed by stirring at room temperature for 4 days. Then, the reaction mixture was diluted with 300 ml of water, adjusted to pH 5 with dil.HCl, and twice extracted with ethyl ether. The extract was washed with water (2 times), dried and evaporated under reduced pressure. The residue was subjected to silica gel column chromatography (solvent: ethyl acetate-hexane=1:1); the resulting product was recrystallized from dichloromethane-hexane=1:10 to yield 2.57 g of methyl ester of 3-0-octadecyl-D-glucosaccharoascorbic acid.

Yield: 29.6%. Melting point: 48°-50° C.

IR (KBr) cm⁻¹. 3550-3100, 1770-1735, 1690.

¹H-NMR (CDCl₃) δ. 0.88(t, 3H), 1.05-1.75(m, 32H), 2.3-3.1(br, OH×2), 3.82(s, 3H), 4.40(t, 2H, J=6 Hz), 4.60(d, 1H, J=2 Hz), 4.98(d, 1H, J=2 Hz). Elemental analysis (%). Calculated for C₂₅H₄₄O₇: C 65.76; H 9.71. Found: C 65.43; H 9.76.

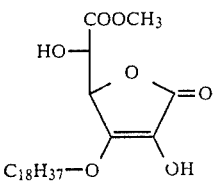

EXAMPLE 11

(n-octadecyl ester of 3-0-octadecyl-D-glucosaccharoascorbic acid)

5.00 g of n-octadecyl ester of D-glucosaccharoascorbic acid was dissolved in 30 ml of dimethylsulfoxide. To this solution were added 1.25 g of potassium carbonate and then a solution of 4.30 g of n-octadecyl iodide in 15 ml of tetrahydrofuran, followed by heating at 60° C. for 6 hours. Then, the reaction mixture was diluted with 400 ml of water and adjusted to pH 3 with dil.HCl, and twice extracted with ethyl ether. The extract was dried and evaporated under reduced pressure. The residue was subjected to silica gel column chromatography (solvent: ethyl acetate-hexane=1:2); the resulting product was recrystallized from dichloromethane-hexane=1:4 to yield 2.23 g of n-octadecyl ester.0.5 hydrate of 3-0-octadecyl-D-glucosaccharoascorbic acid.

Yield: 28.0%. Melting point: 60°-67° C.

IR (KBr) cm⁻¹. 3650-3000, 1765, 1740, 1700.

¹H-NMR (CDCl₃) δ. 0.88(m, 6H), 1.18-1.75(m, 64H), 4.19(t, 2H, J=7 Hz), 4.39(t, 2H, J=6 Hz), 4.57(d, 1H, J=2 Hz), 4.97(d, 1H, J=2 Hz). Figuring for OH is difficult because its band is very broad. Elemental analysis (%). Calculated for C₄₂H₇₈O₇.0.5H₂O: C 71.65; H 11.45. Found: C 71.53; H 11.63.

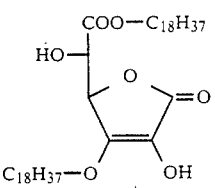

EXAMPLE 12

(Methyl ester of 3-0-benzyl-D-glucosaccharoascorbic acid)

22.2 g of methyl ester.monohydrate of D-glucosaccharoascorbic acid was dissolved in 200 ml of dimethylsulfoxide. To this solution was added 6.9 g of potassium carbonate and then 12.7 g of benzyl chloride dropwise, followed by stirring at about 60° C. for 4 hours. Then, the reaction mixture was diluted with 500 ml of water and extracted with 1 l of ethyl acetate. After water washing, the extract was dried over anhydrous magnesium sulfate. The solvent was distilled off under reduced pressure; the residue was subjected to silica gel column chromatography (solvent: ethyl acetate) to yield 21.0 g of methyl ester of 3-0-benzyl-D-glucosaccharoascorbic acid.

Yield: 71.0%. Oily substance.

IR (liq. film) cm$^{-1}$. 3350, 1750, 1690.

$^1$H-NMR (CDCl$_3$) δ. 3.64(s, 3H), 3.8-4.3(br. 2H), 4.66(d, 1H), 5.06(d, 1H), 5.45(s, 2H), 7.37(s, 5H).

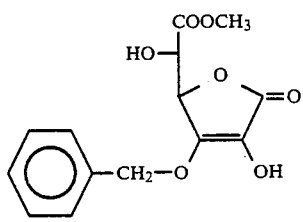

EXAMPLE 13

(Methyl ester of 3-0-benzyl-L-gulosaccharoascorbic acid and methyl ester of 2,3-di-O-benzyl-L-gulosaccharoascorbic acid)

A mixture comprising 196 g of L-gulosaccharoascorbic acid.monohydrate, 5 ml of concentrate HCl and 800 ml of methanol was refluxed with heating for 4 hours. Then, the mixture was evaporated under reduced pressure to yield crude methyl ester of L-gulosaccharoascorbic acid in the form of a viscous liquid. This crude reaction product was dissolved in 800 ml of dimethylsulfoxide. To this solution were added 276 g of potassium carbonate and 242 g of benzyl chloride, followed by stirring at room temperature for 16 hours. Then, the reaction mixture was diluted with 500 ml of water and then thrice extracted with dichloromethane (in total about 3 l of dichloromethane was used). After drying over anhydrous sodium sulfate, the solvent was distilled off under reduced pressure; the obtained residue was fractionally purified by silica gel column chromatography (solvent: dichloromethane) to yield 48.7 g of methyl ester of 3-0-benzyl-L-gulosaccharoascorbic acid and 142 g of methyl ester of 2,3-di-O-benzyl-L-gulosaccharoascorbic acid.

Methyl ester of 3-0-benzyl-L-gulosaccharoascorbic acid: Yield: 17.6%. Oily substance.

IR (liq. film) cm$^{-1}$. 3600-3100, 3050, 1760, 1690.

$^1$H-NMR (CDCl$_3$) δ. 2.94(d, 1H), 3.87(s, 3H), 4.50(m, 1H), 4.88(br. 1H), 4.99(d, 1H), 5.38-5.55(q, 2H), 7.2-7.45(m, 5H). Elemental analysis (%). Calculated for C$_{14}$H$_{14}$O$_7$: C 57.14; H 4.80. Found: C 56.87; H 4.53.

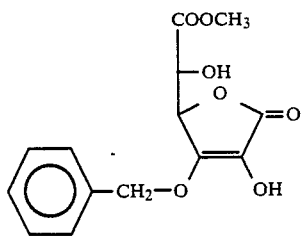

Methyl ester of 2,3-di-O-benzyl-L-gulosaccharoascorbic acid: Yield: 39.2%. Oily substance.

IR (liq. film) cm$^{-1}$. 3600-3200, 3100-2850, 1760, 1680.

$^1$H-NMR (CDCl$_3$) δ. 2.95(d, 1H), 3.84(s, 3H), 4.35-4.50(q, 1H), 4.94(d, 1H), 5.09(s, 2H), 5.05-5.35(q, 2H), 7.20-7.40(m, 10H). Elemental analysis (%). Calculated for C$_{21}$H$_{20}$O$_7$: C 65.62; H 5.24. Found: C 65.68; H 5.32.

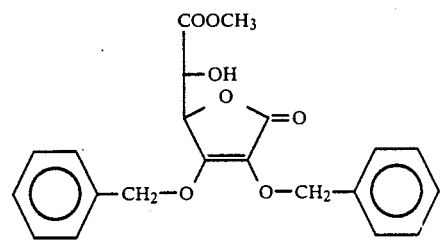

EXAMPLE 14

(Methyl ester of 3-0-benzyl-2-0-heptyl-D-glucosaccharoascorbic acid)

4.02 g of the methyl ester of 3-0-benzyl-D-glucosaccharoascorbic acid produced in Example 12 was dissolved in 30 ml of dimethylsulfoxide. To this solution were added 1.89 g of potassium carbonate and then a solution of 3.24 g of n-heptyl iodide in 30 ml of tetrahydrofuran, followed by stirring at room temperature for 24 hours. Then, the reaction mixture was diluted with 400 ml of water and extracted with dichloromethane five times. The extract was washed (2 times), dried and evaporate under reduced pressure. The residue was subjected to silica gel column chromatography (solvent: ethyl acetate-hexane=1:2) to yield 3.45 g of methyl ester of 3-0-benzyl-2-0-heptyl-D-glucosaccharoascorbic acid.

Yield: 64.4%. Oily substance.

IR (liq. film) cm$^{-1}$. 3600-3250, 1780-1740, 1680.

$^1$H-NMR (CDCl$_3$) δ. 0.88(t, 3H), 1.10-1.84(m, 10H), 2.93(d, OH, J=6 Hz), 3.63(s, 3H), 4.07(t, 2H, J=7 Hz), 4.60(dd, 1H, J=6, 2 Hz), 5.00(d, 1H, J=2 Hz), 5.40(s, 4H), 7.36(s, 5H). M.S m/e 392(M).

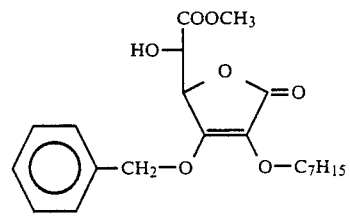

EXAMPLE 15

(Methyl ester of 2-0-heptyl-D-glucosaccharoascorbic acid)

3.24 g of the methyl ester of 3-0-benzyl-2-0-heptyl-D-glucosaccharoascorbic acid produced in Example 14 was dissolved in 50 ml of ethanol. To this solution was added 300 m g of 5% Pt-C, followed by heating to 60° C. and hydrogeneation under atmospheric pressure. After completion of the reaction, the catalyst was removed and the solvent was distilled off to yield 2.49 g of methyl ester of 2-0-heptyl-D-glucosaccharoascorbic acid.

Yield: 100%. Oily substance.

IR (liq. film) cm$^{-1}$. 3650-3100, 1770-1730, 1670.

$^1$H-NMR (DMSO-d$_6$) δ. 0.86(t, 3H), 1.00-1.72(m, 10H), 3.63(s, 3H), 3.85(t, 2H, J=6 Hz), 4.54(d, 1H, J=3 Hz), 4.97(d, 1H, J=3 Hz). Figuring for OH is difficult because its band is very broad. M.S m/e 302(M), 284.

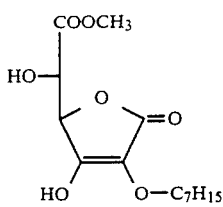

EXAMPLE 16

(3-0-methyl-D-glucosaccharoascorbic acid)

3.36 g of 5,6-0-isopropylidene-3-0-methyl-D-glucosaccharoascorbic acid produced in accordance with Example 4 was added to a mixture of 15 ml of acetic acid and 15 ml of water, followed by heating at 60° C. for 1.5 hours. Then, the solvent was distilled off to yield a crystalline solid. This solid was recrystallized from ethyl acetate-hexane=(10:1) to yield 2.59 g of 3-0-methyl-D-glucosaccharoascorbic acid.

Yield: 92.2%. Melting point: 221°–223° C.

IR (KBr) cm$^{-1}$. 3600–2850, 1740, 1685, 1670.

$^1$H-NMR (DMSO-d$_6$) δ. 3.99(s, 3H), 4.36(d, 1H, J=2 Hz), 4.98(d, 1H, J=2 Hz), 5.4–5.9(br. OH), 8.83(br. OH), 12.2–12.9(br. COOH). Elemental analysis (%). Calculated for C$_7$H$_8$O$_7$: C 41.19; H 3.95. Found: C 41.04; H 3.98.

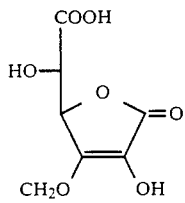

EXAMPLE 17

(2-0-methyl-D-glucosaccharoascorbic acid)

0.20 g of 5,6-0-isopropylidene-3-0-methoxymethyl-2-0-methyl-D-glucosaccharoascorbic acid produced in accordance with Example 6 was added to a mixture of 2 ml of acetic acid and 2 ml of water, followed by heating at 60° C. for 2 hours. Then, the solvent was completely distilled off to yield 0.14 g of 2-0-methyl-D-glucosaccharoascorbic acid.

Yield: 100%. Oily substance.

IR (liq. film) cm$^{-1}$. 3600–2500, 1780–1720, 1680.

$^1$H-NMR (DMSO-d$_6$) δ. 3.64(s, 3H), 4.42(d, 1H, J=2 Hz), 4.96(d, 1H, J=2 Hz). Figuring for OH and CO$_2$H is difficult because their band is very broad. M.S m/e 204(M).

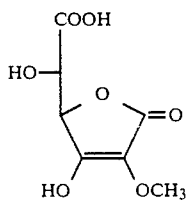

EXAMPLE 18

(3-0-octadecyl-D-glucosaccharoascorbic acid)

3.90 g of 5,6-0-isopropylidene-3-0-octadecyl-D-glucosaccharoascorbic acid produced in accordance with Example 7 was dissolved in a mixture of 8 ml of 2N hydrochloric acid and 32 ml of acetonitrile, followed by heating at 60° C. for 3 hours. Then, the reaction mixture was concentrated under reduced pressure to give a colorless solid. The solid was washed with water, dissolved in a mixture of ethyl acetate and methanol and dried over sodium sulfate. Then, the solvent was distilled off; the residue was recrystallized from ethyl acetate to yield 3.33 g of 3-0-octadecyl-D-glucosaccharoascorbic acid.

Yield: 93.1%. Melting point: 117°–128° C.

IR (KBr) cm$^{-1}$. 3500–3100, 1760, 1750, 1700.

$^1$H-NMR (DMSO-d$_6$) δ. 0.85(t, 3H), 1.10–1.70(m, 32H), 4.30(t, 2H), 4.33(dd, 1H, J=5, 2 Hz), 4.97(d, 1H, J=2 Hz), 5.55(br. OH), 8.70(br. OH). Figuring for CO$_2$H is difficult because its band is very broad. Elemental analysis (%). Calculated for C$_{24}$H$_{42}$O$_7$: C 65.13; H 9.56. Found: C 65.45; H 9.59.

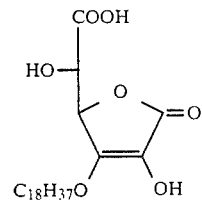

EXAMPLE 19

(3-0-benzyl-2-0-octadecyl-D-glucosaccharoascorbic acid)

2.30 g of 3-0-benzyl-5,6-0-isopropylidene-2-0-octadecyl-D-glucosaccharoascorbic acid produced in accordance with Example 9 was dissolved in a mixture of 10 ml of 2N hydrochloric acid and 40 ml of acetonitrile, followed by heating at 60° C. for 4 hours. Then, the reaction mixture was concentrated under reduced pressure to give a colorless solid. The solid was dissolved in ethyl acetate and twice washed with brine. Then, the organic layer was dried and concentrated under reduced pressure to yield 2.14 g of 3-0-benzyl-2-0-octadecyl-D-glucosaccharoascorbic acid.

Yield: 100%. Melting point: 83°–86° C. (from acetonitrile).

IR (KBr) cm$^{-1}$. 3450, 3400, 3000–2500, 1770, 1730, 1680.

$^1$H-NMR (CDCl$_3$) δ. 0.88(t, 3H), 1.10–1.73(m, 32H), 4.01(t, 2H, J=6 Hz), 4.68(d, 1H, J=2 Hz), 5.08(d, 1H, J=2 Hz), 5.43(s, 2H), 7.34(s, 5H). Figuring for OH and CO$_2$H is difficult because their band is very broad. M.S m/e 532(M), 440. Elemental analysis (%). Calculated for C$_{31}$H$_{48}$O$_7$: C 69.89; H 9.08. Found: C 69.77; H 9.12.

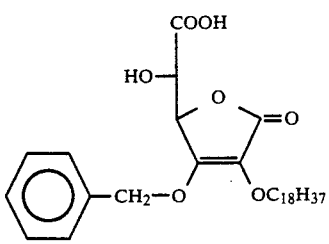

EXAMPLE 20

(2-0-octadecyl-D-glucosaccharoascorbic acid)

2.00 g of 3-0-benzyl-2-0-octadecyl-D-glucosaccharoascorbic acid produced in accordance with Example 19 was dissolved in 25 ml of ethyl acetate, followed by addition of 300 m g of 5% Pd-C and hydrogenation at room temperature under atmospheric pressure. After completion of the reaction, the partially crystallized product was dissolved by addition of methanol and filtered to remove the catalyst. The solvent was distilled off; the resulting crystalline solid was recrystallized from ethyl acetate-hexane=2:1 to yield 1.55 g of 2-0-octadecyl-D-glucosaccharoascorbic acid.

Yield: 93.4%. Melting point: 138°–148° C.

IR (KBr) cm$^{-1}$. 3530, 3300–2900, 1750, 1730, 1660.

$^1$H-NMR (DMSO-d$_6$) δ. 0.85(t, 3H), 1.15–1.65(m, 32H), 3.83(t, 2H, J=6 Hz), 4.40(d, 1H, J=2 Hz), 4.93(d, 1H, J=2 Hz). Figuring for OH and CO$_2$H is difficult because their band is very broad. Elemental analysis (%). Calculated for C$_{24}$H$_{42}$O$_7$: C 65.13; H 9.56. Found: C 65.42; H 9.73.

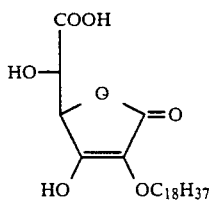

EXAMPLE 21

(n-octadecyl ester of 3-0-benzyl-2-0-octadecyl-D-glucosaccharoascorbic acid)

2.00 g of 3-0-benzyl-2-0-octadecyl-D-glucosaccharoascorbic acid produced in accordance with Example 19 was dissolved in 20 ml of dimethylsulfoxide. To this solution were added 0.31 g of potassium carbonate and then a solution of 1.43 g of n-octadecyl iodide in 20 ml of tetrahydrofuran, followed by stirring at room temperature overnight. Then, the reaction mixture was diluted with 300 ml of water and thrice extracted with ethyl ether. The extract was washed with water (2 times), dried and evaporated under reduced pressure. The residue was subjected to silica gel column chromatography (solvent: ethyl acetate-hexane=1:3) to yield 2.61 g of a crude crystal of n-octadecyl ester of 3-0-benzyl-2-0-octadecyl-D-glucosaccharoascorbic acid.

Yield: 88.6%.

IR (KBr) cm$^{-1}$. 3550–3350, 1765, 1730, 1680.

$^1$H-NMR (CDCl$_3$) δ. 0.88(m, 6H), 1.10–1.76(m, 64H), 3.00(d, OH, J=6 Hz), 4.03(t, 2H, J=7 Hz), 4.06(t, 2H, J=7 Hz), 4.58(dd, 1H, J=6, 2 Hz), 4.99(d, 1H, J=2 Hz), 5.38, 5.40(2H), 7.36(s, 5H). M.S m/e 784(M), 692.

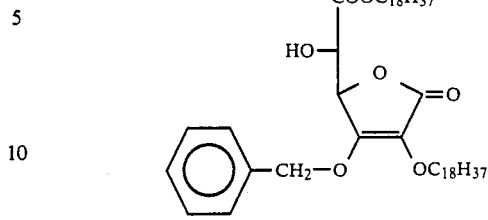

EXAMPLE 22

(n-octadecyl ester of 2-0-octadecyl-D-glucosaccharoascorbic acid)

2.33 g of n-octadecyl ester of 3-0-benzyl-2-0-octadecyl-D-glucosaccharoascorbic acid produced in accordance with Example 21 was dissolved in 60 ml of ethanol. To this solution was added 350 mg of 5% Pt-C, followed by heating to 60° C. and hydrogenation under atmospheric pressure. After completion of the reaction, the catalyst was removed by filtration; the crystalline product which crystallized partially during hydrogenation was dissolved into the mother solution by hot ethyl acetate. The solvent was distilled off; the residue was recrystallized from ethyl acetate to yield 1.82 g of n-octadecyl ester of 2-0-octadecyl-D-glucosaccharoascorbic acid.

Yield: 88.2%. Melting point: 90.5°–91.5° C.

IR (KBr) cm$^{-1}$. 3450–3100, 1750, 1740, 1680.

$^1$H-NMR (CDCl$_3$) δ. 0.88(m, 6H), 1.14–1.80(m, 64H), 4.14(t, 2H, J=6 Hz), 4.25(t, 2H, J=7 Hz), 4.56(d, 1H, J=4 Hz), 4.94(d, 1H, J=4 Hz). Figuring for OH is difficult because its band is very broad. Elemental analysis (%). Calculated for C$_{42}$H$_{78}$O$_7$: C 72.58; H 11.31. Found: C 72.39; H 11.33.

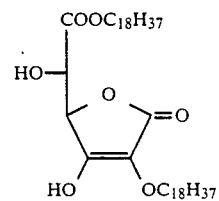

EXAMPLE 23

(n-dodecyl ester of 3-0-benzyl-2-0-octadecyl-D-glucosaccharoascorbic acid)

3.00 g of 3-0-benzyl-2-0-octadecyl-D-glucosaccharoascorbic acid produced in accordance with Example 19 was dissolved in 30 ml of dimethylsulfoxide. To this solution were added 0.47 g of potassium carbonate and then a solution of 1.40 g of n-dodecyl bromide in 30 ml of tetrahydrofuran, followed by stirring at room temperature for 2 days. Then, the reaction mixture was diluted with 400 ml of water and thrice extracted with ethyl ether. The extract was washed with water (2 times), dried and evaporated under reduced pressure. The residue was subjected to silica gel column chromatography (solvent: ethyl acetate-hexane=1:2) to yield 3.30 g of n-dodecyl ester of 3-0-benzyl-2-0-octadecyl-D-glucosaccharoascorbic acid.

Yield: 83.6%. Oily substance.

IR (liq. film) cm$^{-1}$. 3550–3330, 1780–1740, 1685.

$^1$H-NMR (CDCl$_3$) δ. 0.88(t, 3H), 1.07–1.80(m, 52H), 2.97(d, OH, J=6 Hz), 4.03(t, 2H, J=7 Hz), 4.06(t, 2H, J=6 Hz), 4.58(dd, 1H, J=6, 2 Hz), 4.99(d, 1H, J=2 Hz), 5.38, 5.40(2H), 7.35(s, 5H). M.S m/e 700(M), 608.

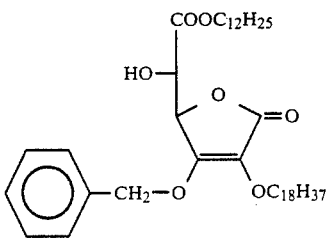

EXAMPLE 24

(n-dodecyl ester of 2-0-octadecyl-D-glucosaccharoascorbic acid)

3.10 g of n-dodecyl ester of 3-0-benzyl-2-0-octadecyl-D-glucosaccharoascorbic acid produced in accordance with Example 23 was dissolved in 50 ml of ethanol. To this solution was added 300 m g of 5% Pt-C, followed by heating to 60° C. and hydrogenation under atmospheric pressure. After completion of the reaction, the catalyst was removed and the solvent was distilled off; the resulting crystalline solid was recrystallized from methanol to yield 2.52 g of n-dodecyl ester of 2-0-octadecyl-D-glucosaccharoascorbic acid.

Yield: 93.3%. Melting point: 76°–78° C.

IR (KBr) cm$^{-1}$. 3400–3100, 1750, 1730, 1680.

$^1$H-NMR (CDCl$_3$) δ. 0.88(m, 6H), 1.10–1.80(m, 52H), 4.14(t, 2H, J=7 Hz), 4.25(t, 2H, J=7 Hz), 4.57(d, 1H, J=4 Hz), 4.95(d, 1H, J=4 Hz). Figuring for OH is difficult because its band is very broad. Elemental analysis (%). Calculated for C$_{36}$H$_{66}$O$_7$: C 70.78; H 10.89. Found: C 70.50; H 10.91.

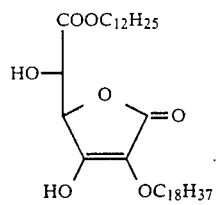

EXAMPLE 25

(N,N-pentamethylene amide of 5-O-acetyl-2,3-di-O-benzyl-D-glucosaccharoascorbic acid)

5.80 g of 5-O-acetyl-2,3-di-O-benzyl-D-glucosaccharoascorbic acid was dissolved in 40 ml of dichloromethane. To this solution was added 3.22 g of phosphorus pentachloride, followed by stirring at room temperature for 30 minutes.

Low boiling point substances were distilled off under reduced pressure to yield a pasty acid chloride. This acid chloride was dissolved in 30 ml of dichloromethane. To this solution, a mixed solution of 1.26 g of piperidine, 1.50 g of triethylamine and 6 ml of dichloromethane was added dropwise, while cooling with ice, followed by stirring for 1 hour.

The reaction mixture was poured into 80 ml of water and thrice extracted with dichloromethane. The extract was dried over sodium sulfate.

After the solvent was distilled off, the residue was subjected to silica gel column chromatography (solvent: ethyl acetate-hexane=1:1) to yield 5.28 g of pasty N,N-pentamethyleneamide of 5-O-acetyl-2,3-di-O-benzyl-D-glucosaccharoascorbic acid.

Yield: 78.1%.

IR (liq. film) cm$^{-1}$. 1770–1750, 1680–1650.

$^1$H-NMR (CDCl$_3$) δ. 1.40–1.70(m, 6H), 1.85(s, 3H), 3.30–3.58(m, 4H), 5.01(d, 1H, J=7 Hz), 5.13(s, 2H), 5.16(z, 2H), 5.58(d, 1H, J=7 Hz), 7.15–7.40(m, 10H). MS m/e 479(M), 419, 388, 328.

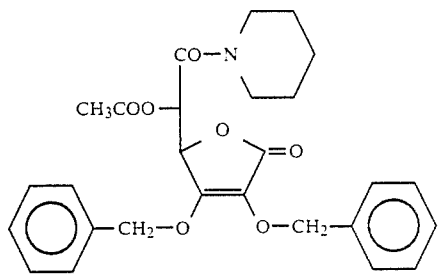

EXAMPLE 26

(N,N-pentamethylene amide of 2,3-di-O-benzyl-D-glucosaccharoascorbic acid)

3.70 g of the N,N-pentamethylene amide of 5-O-acetyl-2,3-di-O-benzyl-D-glucosaccharoascorbic acid produced in Example 25 was dissolved in a mixture of 20 ml of 2N sulfuric acid and 60 ml of acetonitrile; this solution was refluxed with heating for 8 hours.

Then, the acetonitrile was distilled off; the residue was diluted with 50 ml of water and thrice extracted with dichloromethane.

After drying the extract over sodium sulfate, the solvent was distilled off; the resulting residue was subjected to silica gel column chromatography (solvent: ethyl acetate-hexane=1:1) to yield 3.19 g of a crude crystal of N,N-pentamethylene amide of 2,3-di-O-benzyl-D-glucosaccharoascorbic acid.

Yield: 94.5%.

Melting Point: 101°–104° C. (from dichloromethane-hexane).

IR (KBr) cm$^{-1}$. 3450–3300, 1770, 1680, 1645.

$^1$H-NMR (CDCl$_3$) δ. 1.40–1.70(m, 6H), 3.20–3.53(m, 4H), 3.80–4.20(br. OH), 4.66(s, 2H), 4.91(d, 1H, J=11 Hz), 5.15(s, 2H), 5.18(d, 1H, J=11 Hz), 7.16–7.43(m, 10H). MS m/e 437(M), 419, 346, 328. Elemental analysis (%). Calculated for C$_{25}$H$_{27}$NO$_6$: C 68.64; H 6.22; N 3.20. Found: C 68.51; H 6.00; N 3.14.

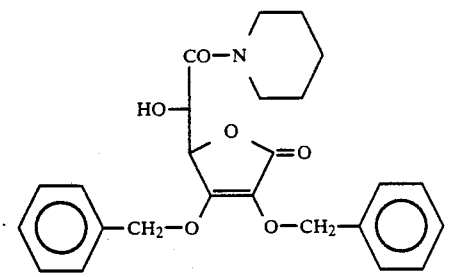

EXAMPLE 27

(n-decylamide of 5-O-acetyl-2,3-di-O-benzyl-D-glucosaccharoascorbic acid)

9.14 g of 5-O-acetyl-2,3-di-O-benzyl-D-glucosaccharoascorbic acid was dissolved in 60 ml of dichloromethane. To this solution was added 5.08 g of phosphorus pentachloride, followed by stirring at room temperature for 1 hour.

Low boiling point substances were distilled off under reduced pressure to yield a pasty acid chloride.

This acid chloride was dissolved in 40 ml of dichloromethane. To this solution, a mixed solution of 3.67 g of n-decylamine, 2.36 g of triethylamine and 10 ml of dichloromethane was added dropwise, while cooling with ice, followed by stirring for 1 hour. The reaction mixture was poured into 100 ml of water and thrice extracted with dichloromethane. The extract was dried over sodium sulfate.

After the solvent was distilled off, the residue was subjected to silica gel column chromatography (solvent: ethyl acetate-hexane=1:2) to yield 11.32 g of pasty n-decylamide of 5-O-acetyl-2,3-di-O-benzyl-D-glucosaccharoascorbic acid.

Yield: 92.6%.

IR (liq. film) cm$^{-1}$. 3450–3250, 1780–1740, 1690–1660.

$^1$H-NMR (CDCl$_3$) δ. 0.88(t, 3H), 1.20–1.35(m, 16H), 2.13(s, 3H), 2.96–3.23(m, 2H), 5.07(d, 1H), 5.09(s, 2H), 5.25(m, 2H), 5.61(d, 1H, J=3 Hz), 5.95(br. NH), 7.17–7.40(m, 10H). MS m/e 551(M), 491, 460, 400.

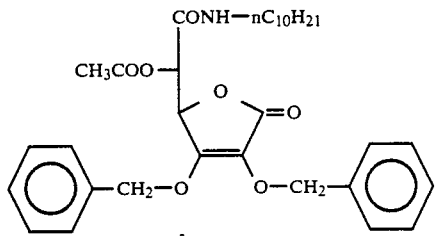

EXAMPLE 28

(n-decylamide of 2,3-di-O-benzyl-D-glucosaccharoascorbic acid)

10.92 g of the n-decylamide of 5-O-acetyl-2,3-di-O-benzyl-D-glucosaccharoascorbic acid produced in Example 27 was dissolved in a mixture of 30 ml of 2N sulfuric acid and 90 ml of acetonitrile; this solution was refluxed with heating for 10 hours.

Then, the acetonitrile was distilled off; the residue was diluted with 80 ml of water and thrice extracted with dichloromethane.

After drying the extract over sodium sulfate, the solvent was distilled off; the resulting residue was subjected to silica gel column chromatography (solvent: ethyl acetate-hexane=1:1) to yield 7.16 g of n-decylamide of 2,3-di-O-benzyl-D-glucosaccharoascorbic acid.

Yield: 71.0%. Melting point: 130°–132° C. (recrystallized from dichloromethanehexane=1:1 mixture).

IR (KBr) cm$^{-1}$. 3400–3250, 1760, 1680, 1650.

$^1$H-NMR (CDCl$_3$) δ. 0.88(t, 3H), 1.10–1.38(m, 16H), 2.64–3.26(m, 2H), 4.33(br. OH), 4.62(dd, 1H, J=5, 2 Hz), 5.05(s, 2H), 5.15(s, 2H), 5.28(d, 1H=2 Hz), 6.67(t, NH), 7.10–7.40(m, 10H). MS m/e 509(M), 481. Elementary Analysis (%) for C$_{30}$H$_{39}$NO$_6$. Calcd.: C, 70.70; H, 7.71; N, 2.75. Found: C, 70.64; H, 7.65; N, 2.70.

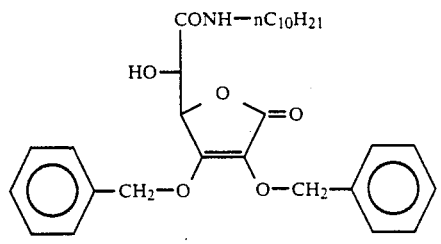

EXAMPLE 29

(n-octadecylamide of 5-O-acetyl-2,3-di-O-benzyl-D-glucosaccharoascorbic acid)

5.00 g of 5-O-acetyl-2,3-di-O-benzyl-D-glucosaccharoascorbic acid was dissolved in 40 ml of dichloromethane. To this solution was added 2.77 g of phosphorus pentachloride, followed by stirring at room temperature for 30 minutes.

Low boiling point substances were distilled off under reduced pressure to yield a pasty acid chloride. This acid chloride was dissolved in 30 ml of dichloromethane. To this solution, a mixed solution of 3.40 g of n-octadecylamine, 1.20 g of triethylamine and 150 ml of dichloromethane was added dropwise, while cooling with ice, followed by stirring for 1 hour.

The reaction mixture was poured into 200 ml of water and thrice extracted with dichloromethane. The extract was dried over sodium sulfate. After the solvent was distilled off, the residue was subjected to silica gel column chromatography (solvent: ethyl acetate-hexane=1:1) to yield 6.10 g of n-octadecylamide of 5-O-acetyl-2,3-di-O-benzyl-D-glucosaccharoascorbic acid.

Yield: 75.8%. Melting point: 51°–53° C. (recrystallized from dichloromethane-hexane=1:4).

IR (KBr) cm$^{-1}$. 3320, 1790, 1750, 1690, 1670.

$^1$H-NMR (DMSO-d$_6$) δ. 0.85(t, 3H), 1.10–1.40(m, 32H), 2.10(s, 3H), 2.90–3.15(m, 2H), 4.94(s, 2H), 5.18–5.40(m, 4H), 7.25–7.42(m, 10H), 8.00(br. NH). Elemental analysis (%). Calculated for C$_{40}$H$_{57}$NO$_7$: C 72.37; H 8.65; N 2.11. Found: C 72.49; H 8.87; N 2.15.

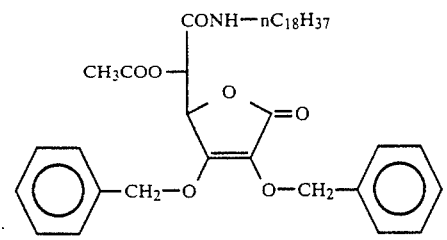

EXAMPLE 30

(n-octadecylamide of 2,3-di-O-benzyl-D-glucosaccharoascorbic acid)

5.90 g of the n-octadecylamide of 5-O-acetyl-2,3-di-O-benzyl-D-glucosaccharoascorbic acid produced in Example 29 was dissolved in a mixture of 20 ml of 2N sulfuric acid and 60 ml of acetonitrile; this solution was refluxed with heating for 12 hours.

Then, the acetonitrile was distilled off; the residue was diluted with 200 ml of water and thrice extracted with dichloromethane. After drying the extract over sodium sulfate, the solvent was distilled off; the resulting residue was subjected to silica gel column chromatography (solvent: ethyl acetate-hexane = 1:1) to yield 3.50 g of n-octadecylamide of 2,3-di-O-benzyl-D-glucosaccharoascorbic acid.

Yield: 63.3%. Melting point: 105°–107° C.

IR (KBr) cm$^{-1}$. 3500–3200, 1755, 1675, 1645.

$^1$H-NMR (DMSO-d$_6$) δ. 0.85(t, 3H), 1.04–1.28(m, 32H), 2.83–3.03(m, 2H), 4.30(m, 1H), 4.95(s, 2H), 5.10–5.20(m, 3H), 6.37(d, OH), 7.18–7.42(m, 10H), 7.66(br. NH). Elemental analysis (%). Calculated for C$_{38}$H$_{55}$NO$_6$: C 73.40; H 8.91; N 2.25. Found: C 73.62; H 8.93; N 2.22.

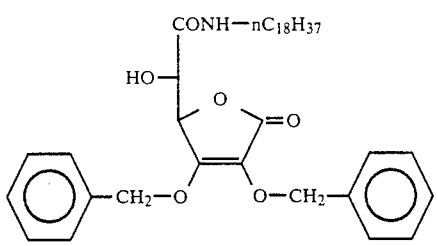

EXAMPLE 31

(n-octadecylamide of 2,3-di-O-benzyl-D-glucosaccharoascorbic acid)

0.80 g of 2,3-di-O-benzyl-5,6-O-isopropylidene-D-glucosaccharoascorbic acid was dissolved in 30 ml of toluene. To this solution was added 0.63 g of n-octadecylamine; this mixture was refluxed with heating for 18 hours.

The solvent was distilled off from the reaction mixture; the resulting residue was subjected to silica gel column chromatography (solvent: ethyl acetate-hexane = 1:2) to yield 0.23 g of n-octadecylamide of 2,3-di-O-benzyl-D-glucosaccharoascorbic acid.

Yield: 19.0%.

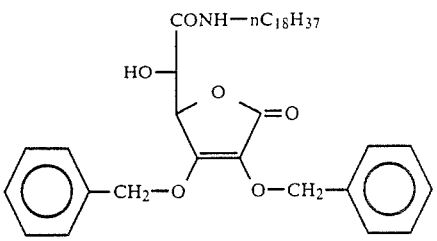

EXAMPLE 32

(Amide of 5-O-acetyl-2,3-di-O-benzyl-D-glucosaccharoascorbic acid)

5.00 g of 5-O-acetyl-2,3-di-O-benzyl-D-glucosaccharoascorbic acid was dissolved in 40 ml of dichloromethane. To this solution was added 2.77 g of phosphorus pentachloride, followed by stirring at room temperature for 30 minutes.

Low boiling point substances were distilled off under reduced pressure to yield a pasty acid chloride. This acid chloride was dissolved in 30 ml of dichloromethane. To this solution, a mixed solution of 7.3 ml of 3% (w/v) ammonia-dichloromethane, 1.21 g of triethylamine and 50 ml of dichloromethane was added dropwise, while cooling with ice, followed by stirring for 1 hour.

The reaction mixture was poured into 150 ml of water and thrice extracted with dichloromethane. The extract was dried over sodium sulfate.

After the solvent was distilled off, the residue was subjected to silica gel column chromatography (solvent: ethyl acetate-hexane = 1:1) to yield 3.50 g of amide of 5-O-acetyl-2,3-di-O-benzyl-D-glucosaccharoascorbic acid.

Yield: 70.1%. Melting point: 140°–142° C.

IR (KBr) cm$^{-1}$. 3470, 3300–3050, 1770, 1760, 1690, 1675.

$^1$H-NMR (DMSO-d$_6$) δ. 2.10(s, 3H), 4.94(s, 2H), 5.17–5.35(m, 4H), 7.23–7.45(m, 10H), 7.55(br. NH$_2$). Elemental analysis (%). Calculated for C$_{22}$H$_{21}$NO$_7$: C 64.23; H 5.14; N 3.40. Found: C 64.05; H 5.15; N 3.39.

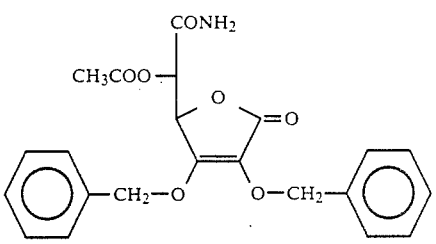

PRODUCTION EXAMPLE 33

(Amide of 2,3-di-O-benzyl-D-glucosaccharoascorbic acid)

3.00 g of the amide of 5-O-acetyl-2,3-di-O-benzyl-D-glucosaccharoascorbic acid produced in Example 32 was dissolved in a mixture of 20 ml of 2N sulfuric acid and 60 ml of acetonitrile; this solution was refluxed with heating for 12 hours.

Then, the acetonitrile was distilled off; the residue was diluted with 150 ml of water and thrice extracted with dichloromethane.

After drying the extract over sodium sulfate, the solvent was distilled off; the resulting residue was subjected to silica gel column chromatography (solvent: ethyl acetate) to yield 2.10 g of amide of 2,3-di-O-benzyl-D-glucosaccharoascorbic acid.

Yield: 78.1%. Melting point: 160°-163° C.
IR (KBr) cm$^{-1}$. 3600-3100, 1780, 1760, 1680, 1650.
$^1$H-NMR (DMSO-d$_6$) δ. 4.30(dd, 1H, J=6, 2 Hz), 4.95(s, 2H), 5.10-5.26(m, 3H), 6.29(d, OH, J=6 Hz), 7.18-7.50(m, 10H), 7.68(br. NH$_2$). Elemental analysis (%). Calculated for C$_{20}$H$_{19}$NO$_6$: C 65.03; H 5.18; N 3.79. Found: C 65.10; H 5.23; N 3.75.

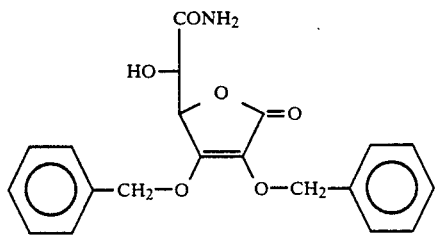

EXAMPLE 34

(N,N-pentamethyleneamide of D-glucosaccharoascorbic acid)

3.79 g of the N,N-pentamethyleneamide of 2,3-di-O-benzyl-D-glucosaccharoascorbic acid produced in Example 26 was dissolved in 50 ml of methanol. To this solution was added 400 mg of 5% Pd-C, followed by hydrogenation at room temperature under atmospheric pressure.

After completion of the reaction, the catalyst was removed by filtration and the methanol was distilled off; the resulting crystalline solid was recrystallized from methanol-dichloromethane-hexane=1:1:1 to yield 1.80 g of N,N-pentamethyleneamide of D-glucosaccharoascorbic acid.

Yield: 80.8%. Melting point: 178° C. <(decomposed).
IR (KBr) cm$^{-1}$. 3500, 3600-2600, 1780, 1720, 1605.
$^1$H-NMR (DMSO-d$_6$) δ. 1.30-1.70(m, 6H), 3.35-3.65(m, 4H), 4.84(d, 1H, J=2 Hz), 4.93(d, 1H, J=2 Hz), 5.70-6.30(br. OH), 7.95-8.85(br. OH), 11.30(s, OH). Elemental analysis (%). Calculated for C$_{11}$H$_{15}$NO$_6$: C 51.36; H 5.88; N 5.44. Found: C 51.08; H 5.82; N 5.45.

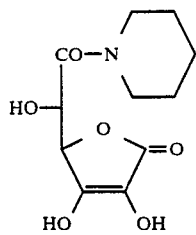

EXAMPLE 35

(n-decylamide of D-glucosaccharoascorbic acid)

6.86 g of the n-decylamide of 2,3di-O-benzyl-D-glucosaccharoascorbic acid produced in Example 28 was dissolved in 80 ml of ethyl acetate. To this solution was added 500 mg of 5% Pd-C, followed by hydrogenation at room temperature under atmospheric pressure.

After completion of the reaction, the catalyst was removed by filtration and the ethyl acetate was distilled off; the resulting crystalline solid was washed with hexane to yield 4.33 g of n-decylamide of D-glucosaccharoascorbic acid.

Yield: 97.7%. Melting point: 138°-143° C.
IR (KBr) cm$^{-1}$. 3470, 3600-2800, 1790, 1700, 1620.
$^1$H-NMR (DMSO-d$_6$) δ. 0.86(t, 3H), 1.10-1.65(m, 16H), 3.05(q, 2H, J=6 Hz), 4.27(m, 1H), 4.92(d, 1H, J'2 Hz), 6.13(d, OH, J=5 Hz), 7.80(t, NH, J=6 Hz), 8.27(br. OH), 11.05(br. OH). Elemental analysis (%). Calculated for C$_{16}$H$_{27}$NO$_6$: C 58.34; H 8.26; N 4.25. Found: C 58.00; H 8.24; N 4.27.

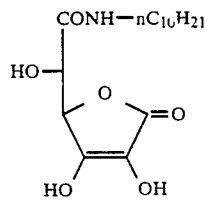

EXAMPLE 36

(n-octadecylamide of D-glucosaccharoascorbic acid)

3.00 g of the n-octadecylamide of 2,3-di-O-benzyl-D-glucosaccharoascorbic acid produced in Example 30 or 31 was dissolved in 60 ml of ethyl acetate. To this solution was added 300 mg of 5% Pd-C, followed by hydrogenation at room temperature under atmospheric pressure.

After completion of the reaction, the catalyst was removed by filtration and the ethyl acetate was distilled off; the resulting crystalline solid was recrystallized from ethyl acetate-hexane=2:3 to yield 1.53 g of n-octadecylamide of D-glucosaccharoascorbic acid.

Yield: 74.8%. Melting point: 96°-98° C.
IR (KBr) cm$^{-1}$. 3600-2700, 1760, 1680, 1650.
$^1$H-NMR (DMSO-d$_6$) δ. 0.85(t, 3H), 1.05-1.35(m, 32H), 2.85-3.18(m, 2H), 4.26(m, 1H), 4.92(d, 1H, J=2 Hz), 6.08(br. OH), 7.77(br. NH), 8.22(br. OH), 11.00(br. OH). Elemental analysis (%). Calculated for C$_{24}$H$_{43}$NO$_6$: C 65.28; H 9.81; N 3.17. Found: C 65.08; H 9.83; N 3.14.

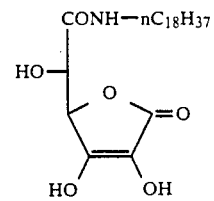

EXAMPLE 37

(Amide of D-glucosaccharoascorbic acid)

1.50 g of the amide of 2,3-di-O-benzyl-D-glucosaccharoascorbic acid produced in Example 33 was dissolved in 80 ml of methanol. To this solution was added 150 mg of 5% Pd-C, followed by hydrogenation at room temperature under atmospheric pressure.

After completion of the reaction, the catalyst was removed by filtration and the methanol was distilled off to yield 0.76 g of D-glucosaccharoascorbic acid amide-0.5 hydrate.

Yield: 94.6%. Melting point: 170°–175° C.

IR (KBr) cm$^{-1}$. 3470, 3600–2400, 1740, 1680–1620.

$^1$H-NMR (DMSO-d$_6$) δ. 4.23(m, 1H), 4.93(d, 1H, J=2 Hz), 6.03(br. OH), 7.26(br. NH$_2$), 8.25(br. OH), 10.95(br. OH). Elemental analysis (%). Calculated for C$_6$H$_7$NO$_6$.0.5H$_2$O: C 36.37; H 4.07; N 7.07. Found: C 36.25; H 3.81; N 6.87.

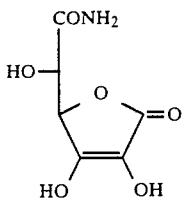

EXAMPLE 38

(5-O-acetyl-3-O-benzyl-2-O-octadecy-D-glucosaccharoascorbic acid)

One drop of concentrated sulfuric acid was added to a mixture of 5.00 g of 3-O-benzyl-2-O-octadecyl-D-glucosaccharoascorbic acid produced in accordance with Example 19, 1.15 g of acetic anhydride and 100 ml of dichloromethane, followed by stirring at room temperature for 2 hours.

Then, the mixture was evaporated in vacuo. The residue was recrystallized from a mixture of dichloromethane and hexane (=1:10) to yield 5.01 g of 5-O-acetyl-3-O-benzyl-2-O-octadecyl-D-glucosaccharoascorbic acid.

Yield: 92.8%. Melting point: 74°–75° C.

IR (KBr) cm$^{-1}$3600–300, 1760, 1710, 1680.

$^1$H-NMR (CDCl$_3$) δ0.88(t, 3H), 1.00–1.80(m, 32H), 2.12(s, 3H), 3.62(br. OH), 4.02(t, 2H, J=7 Hz), 5.13(d, 1H, J=3 Hz), 5.44(s, 2H), 5.61(d, 1H, J=3 Hz), 7.35(s, 5H). Elementary analysis (%). Calcd. for C$_{33}$H$_{50}$O$_8$: C, 68.96; H, 8.77. Found: C, 68.78; H, 8.76.

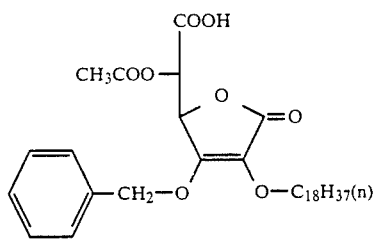

EXAMPLE 39

(n-Octadecyl amide of 5-O-acetyl-3-O-benzyl-2-O-octadecyl-D-glucosaccharoascorbic acid)

2.00 g of 5-O-acetyl-3-O-benzyl-2-O-octadecy-D-glucosaccharoascorbic acid produced in accordance with Example 38 was dissolved in 15 ml of dichloromethane. To this solution was added 0.78 g of phosphorus pentachloride, followed by stirring at room temperature for 1 hour.

Lower boiling point substances were distilled off in vacuo to obtain pasty acid chloride.

The obtained acid chloride was dissolved in 15 ml of dichloromethane, and then, a mixed solution of 0.99 g of n-octadecylamine, 0.37 g of triethylamine and 3 ml of dichloromethane was added dropwise to the solution, followed by stirring in an ice bath for 1 hour. The reaction mixture was poured into 100 ml of water, and extracted with dichloromethane three times. The extract was dried over sodium sulfate. After removing a solvent, the residue was subjected to silica gel column chromatography (solvent: ethyl acetate:hexane=1.5), followed by recrystallized from ethanol to yield 2.33 g of n-octadecylamide of 5-O-acetyl-3-O-benzyl-2-O-octadecy-D-glucosaccharoascorbic acid.

Yield: 81.0%. Melting point: 40°–40.5° C.

IR (KBr) cm$^{-1}$3450–3250, 1760, 1675.

$^1$H-NMR (CDCl$_3$) δ0.88(t, 3H), 1.08–1.05(m, 64H), 2.15(s, 3H), 2.96–3.27(m, 2H), 4.03(t, 2H, J=7 Hz), 5.05(d, 1H, J=3 Hz), 5.47(s, 2H), 5.61(d, 1H, J=3 Hz), 5.96(m, NH), 7.38(s, 5H). Elementary analysis (%). Calcd. for C$_{51}$H$_{87}$NO$_7$: C, 74.14; H, 10.61; N, 1.70. Found: C, 74.46; H, 10.69; N, 1.65.

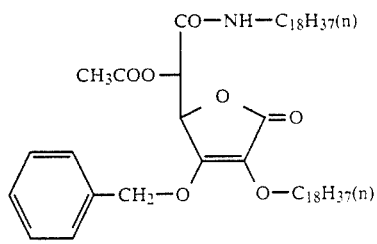

EXAMPLE 40

(n-Octadecylamide of 3-O-benzyl-2-O-octadecyl-D-glucosaccharoascorbic acid)

1.37 g of n-octadecylamide of 5-O-acetyl-3-O-benzyl-2-O-octadecyl-D-glucosaccharoascorbic acid produced in accordance with Example 39 was dissolved in a mixture of 15 ml of 2N sulfuric acid and 100 ml of acetonitrile, followed by refluxing with heating for 6 hours.

Colorless crystals from the reaction mixture was filtered off, washed with acetonitrile, and recrystallized from ethyl acetate to yield 1.12 g of n-Octadecylamide of 3-O-benzyl-2-O-octadecyl-D-glucosaccharoascorbic acid.

Yield: 86.0%. Melting point: 107°–109° C.

IR (KBr) cm$^{-1}$3500–3200, 1760, 1680, 1660.

$^1$H-NMR (CDCl$_3$) δ0.88(t, 3H), 1.05–1.40(m, 64H), 2.80–3.30(m, 2H), 3.63(br. OH), 4.01(t, 2H, J=6 Hz), 4.57(m, 1H), 5.26(m, 1H), 5.43(s, 2H), 6.60(m, NH), 7.34(s, 5H). Elementary analysis (%). Calcd. for C$_{49}$H$_{85}$NO$_6$: C, 75.05; H, 10.92; N, 1.79. Found: C, 75.48; H, 10.98; N, 1.72.

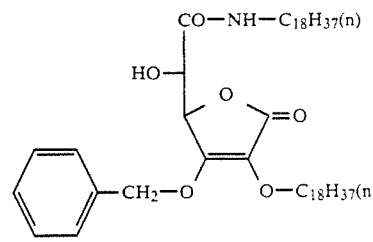

EXAMPLE 41

(n-Octadecylamide of 5-O-acetyl-2-O-octadecyl-D-glucosaccharoascorbic acid)

0.55 g of n-Octadecylamide of 5-O-acetyl-3-O-benzyl-2-O-octadecyl-D-glucosaccharoascorbic acid produced in accordance with Example 39 was dissolved in 20 ml of ethyl acetate. To this solution was added 60 mg of 5% Pd-C, followed by hydrogenation at room temperature under atmospheric pressure.

After completion of the reaction, the catalyst was removed by filtration, and the solvent was distilled off. The obtained crystalline solid was recrystallized from ethyl acetate to yield 0.40 g of n-Octadecyl amide of 5-O-acetyl-2-O-octadecyl-D-glucosaccharoascorbic acid.

Yield: 81.6%. Melting point: 104°–106° C.

IR (KBr) cm$^{-1}$3400, 1770, 1740, 1675, 1630.

$^1$H-NMR (CDCl$_3$) δ0.88(t, 3H), 1.10–1.55(m, 64H), 2.12(s, 3H), 3.28(m, 2H), 4.15(t, 2H, J=6 Hz), 4.98(d, 1H, J=2 Hz), 5.60(d, 1H, J=2 Hz), 6.90(m, NH). Elementary analysis (%). Calcd. for $C_{44}H_{81}NO_7$: C, 71.79; H, 11.09; N, 1.90. Found: C, 72.26; H, 11.32; N, 1.94.

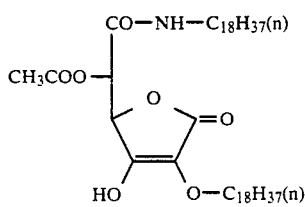

EXAMPLE 42

(n-octadecanethiolester of 5-Oacetyl-2,3-di-O-benzyl-D-glucosaccharoascorbic acid)

4.89 g of 5-O-acetyl-2,3-di-O-benzyl-D-glucosaccharoascorbic acid was dissolved in 30 ml of dichloromethane. To this solution was added 2.59 g of phosphorus pentachloride, followed by stirring at room temperature for 30 minutes.

Low boiling point substances were distilled off under reduced pressure to yield a pasty acid chloride.

This acid chloride was dissolved in 20 ml of dichloromethane. To this solution, a solution of 3.40 g of n-octadecyl mercaptan in 5 ml of dichloromethane were added dropwise, while cooling with ice.

Then, a mixture of 1.20 g of triethylamine and 3 ml of dichloromethane was gradually added dropwise, followed by stirring for 4 hours.

The reaction mixture was poured into 100 ml of water and thrice extracted with dichloromethane. The extract was dried over sodium sulfate. After the solvent was distilled off, the residue was subjected to silica gel chromatography (solvent: ethyl acetate-hexane=1:5) to yield 2.97 g of n-octadecanethiolester of 5-O-acetyl-2,3-di-O-benzyl-D-glucosaccharoascorbic acid.

Yield: 36.8%. Melting point: 61°–62° C. (from hexane).

IR (KBr) cm$^{-1}$1770, 1750, 1685, 1670.

$^1$H-NMR (CDCl$_3$) δ: 0.88(t, 3H), 1.10–1.60(m, 32H), 2.16(s, 3H), 2.74(t, 2H), 5.09(s, 2H), 5.11(d, 1H), 5.20(s, 2H), 5.72(d, 1H, J=3 Hz), 7.13–7.38(m, 10H). MS m/e 680(M), 620, 588. Elemental analysis (%). Calcd. for $C_{40}H_{56}O_7S$: C, 70.55; H, 8.29. Found: C, 70.47; H, 8.27.

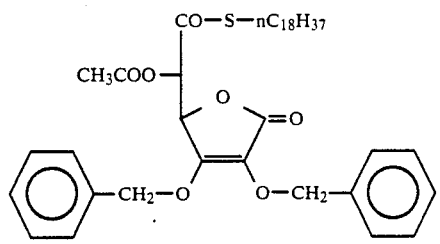

EXAMPLE 43

(n-octadecanethiolester of 2,3-di-O-benzyl-D-glucosaccharoascorbic acid)

The 2.97 g of n-octadecanethiolester of 5-O-acetyl-2,3-di-O-benzyl-D-glucosaccharoascorbic acid was dissolved in a mixture of 20 ml of 2N sulfuric acid and 100 ml of acetonitrile; this solution was refluxed with heating for 20 hours. After completion of the reaction, the acetonitrile was distilled off; the residue was diluted with 50 ml of water and thrice extracted with dichloromethane.

After drying the extract, the solvent was distilled off; the resulting residue was subjected to silica gel column chromatography (solvent: ethyl acetate-hexane=1:5) to yield 2.67 g of n-octadecanethiolester of 2,3-di-O-benzyl-D-glucosaccharoascorbic acid.

Yield: 95.8%. Melting point: 55°–56° C. (from hexane).

IR (KBr) cm$^{-1}$3600–3300, 1770, 1670.

$^1$H-NMR (CDCl$_3$) δ0.88(t, 3H), 1.08–1.53(m, 32H), 2.68(m, 2H), 4.67(d, 1H, J=2 Hz), 5.00–5.17(m, 5H), 7.09–7.38(m, 10H).

Numerical representation for OH was difficult due to the extremely broad assignment pattern.

Elemental analysis (%). Calcd. for $C_{38}H_{54}O_6S$: C, 71.44; H, 8.52. Found: C, 71.45; H, 8.56.

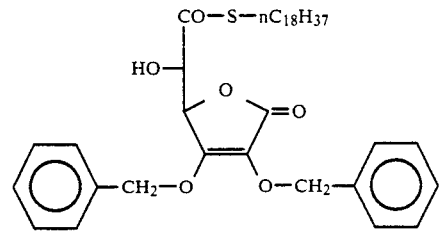

EXAMPLE 44

(Benzenethiolester of 5-O-acetyl-2,3-di-O-benzyl-D-glucosaccharoascorbic acid)

1.00 g of 5-O-acetyl-2,3-di-O-benzyl-D-glucosaccharoascorbic acid was dissolved in 20 ml of dry dichloromethane. To this solution was added 1.06 g of triphenylphosphine dibromide, followed by stirring at room temperature for 5 minutes. Then, 0.27 g of thiophenol was added, followed by stirring for 10 minutes. To this mixture, 0.19 g of pyridine was added dropwise, followed by stirring at room temperature for 3 hours.

The reaction mixture was poured into 100 ml of water and thrice extracted with dichloromethane. The extract was dried over sodium sulfate.

After the solvent was distilled off, the residue was subjected to silica gel column chromatography (solvent: ethyl acetate-hexane = 1:4) to yield 0.82 g of pasty benzenethiolester of 5-O-acetyl-2,3-di-O-benzyl-D-glucosaccharoascorbic acid.

Yield: 67.2%.

IR (liq. film) cm$^{-1}$ 1760, 1680.

$^1$H-NMR (CDCl$_3$) $\delta$2.23(s, 3H), 5.12(s, 2H), 5.15(d, 1H), 5.20(s, 2H), 5.84(d, 1H, J=3 Hz), 7.00–7.41(m, 15H). Elemental analysis (%). Calcd. for C$_{28}$H$_{24}$O$_7$S: C, 66.65; H, 4.79. Found: C, 66.63; H, 4.84.

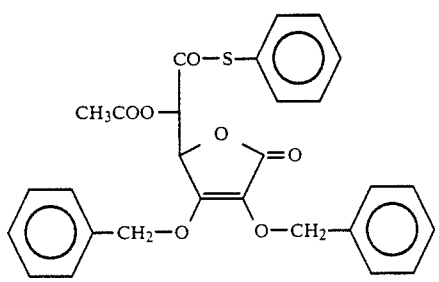

EXAMPLE 45

(Benzenethiolester of 2,3-di-O-benzyl-D-glucosaccharoascorbic acid)

0.71 g of the benzenethiolester of 5-O-acetyl-2,3-di-O-benzyl-D-glucosaccharoascorbic acid was dissolved in a mixture of 4 ml of 2N sulfuric acid and 20 ml of acetonitrile. This solution was refluxed with heating for 6 hours.

After completion of the reaction, the acetonitrile was distilled off. The resulting residue was diluted with 50 ml of water and thrice extracted with dichloromethane.

After drying the extract with sodium sulfide, the solvent was distilled off. The resulting residue was subjected to silica gel column chromatography (solvent: ethyl acetate-hexane = 1:3). The obtained product was recrystallized from dichloromethane-hexane = 1:5 to yield 0.51 g of benzenethiolester of 2,3-di-O-benzyl-D-glucosaccharoascorbic acid.

Yield: 78.2% Melting point: 116°–118° C.

IR (KBr)cm$^{-1}$ 3600–3200, 1770, 1680.

$^1$H-NMR (CDCl$_3$) $\delta$3.82(d, OH, J=7 Hz), 4.82(dd, 1H, J=7, 2 Hz), 5.05–5.20(m, 5H), 6.88–7.45(m, 15H). Elemental analysis (%), Calcd. for C$_{26}$H$_{22}$O$_6$S: C 67.52; H 4.79. Found: C 67.52; H 4.81.

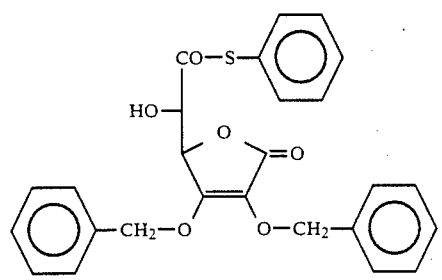

EXAMPLE 46

(n-octadecanethiolester of D-glucosaccharoascorbic acid)

0.80 g of the n-octadecanethiolester of 2,3-di-O-benzyl-D-glucosaccharoascorbic acid was dissolved in 12 ml of dichloromethane. To this solution was added 0.98 g of tin tetrachloride, followed by stirring at room temperature for 2 days.

After completion of the reaction, the reaction mixture was diluted with 50 ml of ethyl acetate and then washed with a brine four times.

After the organic layer was dried and concentrated under reduced pressure, the residue was subjected to silica gel column chromatography (solvent: ethyl acetate). The obtained product was recrystallized from ethyl acetate-methanol = 1:1 to yield 0.05 g of n-octadecanethiolester of D-glucosaccharoascorbic acid.

Yield: 8.8%. Melting point: 96°–100° C.

IR (KBr)cm$^{-1}$ 3600–2800, 1740, 1660, 1640.

$^1$H-NMR (DMSO-d$_6$) $\delta$0.85(t, 3H), 1.05–1.55(m, 32H), 2.73(t, 2H, J=7 Hz), 4.47(m, 1H), 4.92(d, 1H, J=2 Hz), 6.68(br. OH), 8.37(br. OH), 11.10(br. OH).

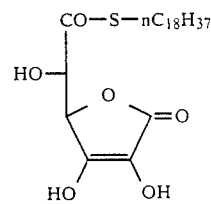

EXAMPLE 47

(Benzenethiolester of D-glucosaccharoascorbic acid)

0.20 g of the benzenethiolester of 2,3-di-O-benzyl-D-glucosaccharoascorbic acid was dissolved in 5 ml of dichloromethane. To this solution was added 0.35 g of tin tetrachloride, followed by stirring at room temperature overnight.

After completion of the reaction, the reaction mixture was diluted with 40 ml of ethyl acetate and then washed with a brine four times.

After the organic layer was dried and concentrated under reduced pressure, the residue was subjected to silica gel column chromatography (solvent: ethyl acetate) to yield 0.08 g of pasty benzenethiolester of D-glucosaccharoascorbic acid.

Yield: 65.9%.

IR (liq. film)cm$^{-1}$ 3600–2800, 1740, 1680–1640.

$^1$H-NMR (DMSO-d$_6$) $\delta$4.62(m, 1H), 4.95(d, 1H, J=2 Hz), 6.90(br. OH), 7.20–7.55(m, 5H), 8.40(br. OH), 11.26(br. OH).

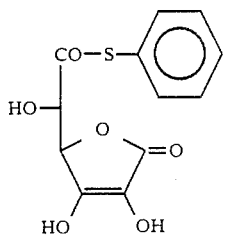

EXAMPLE 48

(5,6-O-isopropylidene-2,3-di-O-methyl-D-glucosaccharoascorbic acid)

2.00 g of 5,6-O-isopropylidene-D-glucosaccharoascorbic acid produced in accordance with Example 1 was dissolved in 15 ml of dimethylsulfoxide. To this solution was added 2.40 g of potassium carbonate, followed by dropwise addition of 4.94 g of methyl iodide and stirring at room temperature for 1 hour.

Then, the remaining insoluble salt was removed by filtration. The filtrate was diluted with 200 ml of water and extracted with dichloromethane three times. The extract was washed with water (4 times), dried and evaporated under reduced pressure. The residue was subjected to silica gel column chromatography (solvent; ethyl acetate: hexane=1:1). The resulting product was recrystallized from a mixture of ethyl acetate and hexane (=1:1) to yield 1.22 g of 5,6-O-isopropylidene-2,3-di-O-methyl-D-glucosaccharoascorbic acid.

Yield: 54.3%. Melting point: 128°–129° C.

IR (KBr)cm$^{-1}$ 1800, 1765, 1680.

$^1$H-NMR (CDCl$_3$) δ1.57(s, 3H), 1.63(s, 3H), 3.86(s, 3H), 4.16(s, 3H), 4.78(d, 1H, J=2 Hz), 4.93(d, 1H, J=2 Hz). MS m/e 258(M), 243

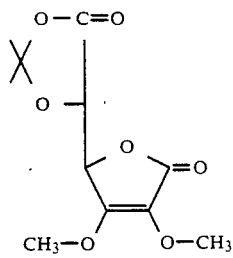

EXAMPLE 49

(2,3-di-O-methyl-D-glucosaccharoascorbic acid)

2.81 g of 5,6-O-isopropylidene-2,3-di-O-methyl-D-glucosaccharoascorbic acid produced in accordance with Example 48 was added to a mixture of 15 ml of acetic acid and 15 ml of water, followed by heating to 60° C. for 1.5 hours.

Then, a solvent was distilled to obtain a crystalline solid. The crystalline solid was dissolved in 80 ml of hot ethyl acetate. To this solution was added 20 ml of hexane to recrystallize the resulting product. 2.26 g of 2,3-di-O-methyl-D-glucosaccharoascorbic acid was obtained.

Yield: 95.2%. Melting point: 161°–163° C.

IR (KBr)cm$^{-1}$ 3400, 3200–2800, 1750, 1720, 1670.

$^1$H-NMR (DMSO-db) δ3.70(s, 3H), 4.02(s, 3H), 4.39(d, 1H, J=2 Hz), 5.05(d, 1H, J=2 Hz), 5.5–6.0(br. OH), 12.5–13.4(br, CO$_2$H). Elementary analysis (%). Calcd. for C$_8$H$_{10}$O$_7$: C, 44.04; H, 4.62. Found: C, 43.74; H, 4.60.

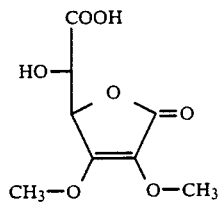

EXAMPLE 50

(5-O-acetyl-2,3-di-O-methyl-D-glucosaccharoascorbic acid)

0.94 g of the title compound (½CH$_3$COOH) was produced from 0.80 g of 2,3-di-O-methyl-D-glucosaccharoascorbic acid as a starting material by a similar method to Example 38.

Yield: 88.3%. Melting point: 131°–134° C.

IR (KBr)cm$^{-1}$ 3600–2800, 1775, 1765, 1745, 1670.

$^1$H-NMR (DMSO-db) δ2.10(s, 3H), 3.71(s, 3H), 4.08(s, 3H), 5.28(d, 1H, J=2 Hz), 5.32(d, 1H, J=2 Hz) Elementary analysis (%). Calcd. for C$_{10}$H$_{12}$O$_8$·½CH$_3$COOH: C, 45.52; H, 4.86. Found: C, 45.53; H, 4.58.

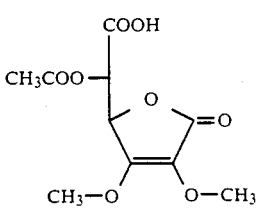

EXAMPLE 51

(3-O-benzyl-D-glucosaccharoascorbic acid)

10.0 g of methyl ester of 3-O-benzyl-D-glucosaccharoascorbic acid was dissolved in 200 ml of acetic acid. To this solution was added 20 ml of concentrated hydrochloric acid, and the mixture was allowed to stand at room temperature for 48 hours.

Then, hydrochloric acid and acetic acid were removed. The obtained oil was crystallized from a mixture of ethyl acetate and chloroform to yield 4.80 g of 3-O-benzyl-D-glucosaccharoascorbic acid.

Yield: 50.4%. Melting point: 174° C.

IR (KBr)cm$^{-1}$ 3600–2500, 3380, 1775, 1740, 1710, 1670, 1655.

$^1$H-NMR (DMSO-db) δ4.42(d, 1H, J=2 Hz), 5.05(d, 1H, J=2 Hz), 5.37(d, 1H, J=12 Hz), 5.43(d, 1H, J=12 Hz), 7.38(s, 5H), 9.00(br, CO$_2$H). Elementary analysis (%). Calcd. for C$_{13}$H$_{12}$O$_7$: C, 55.72; H, 4.32. Found: C, 54.97; H, 4.25.

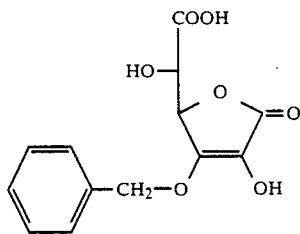

EXAMPLE 52

(2,5-di-O-acetyl-3-O-benzyl-D-glucosaccharoascorbic acid)

One drop of concentrated sulfuric acid was added to a mixture of 0.84 g of 3-O-benzyl-D-glucosaccharoascorbic acid produced in accordance with Example 51, 0.76 g of acetic anhydride and 25 ml of dichloromethane, followed by stirring at room temperature for 4 hours.

Then, the mixture was evaporated under reduced pressure. The residue was subjected to silica gel column chromatography (solvent; ethyl acetate). The obtained product was recrystallized from a mixture of dichloromethane and hexane (=1:2) to yield 0.73 g of 2,5-di-O-acetyl-3-O-benzyl-D-glucosaccharoascorbic acid.

Yield: 66.8%. Melting point: 143°–146° C.
IR (KBr)cm$^{-1}$ 3600–2700, 1765, 1740, 1680.
$^1$H-NMR (CDCl$_3$) δ2.16(s, 3H), 2.19(s, 3H), 4.75(br. OH), 5.27(d, 1H, J=2 Hz), 5.30(s, 2H), 5.68(d, 1H, J=2 Hz), 7.35(m, 5H). Elementary analysis (%). Calcd. for C$_{17}$H$_{16}$O$_9$: C, 56.05; H, 4.43. Found: C, 56.03; H, 4.41.

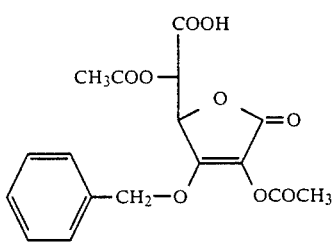

EXAMPLE 53

(5-O-acetyl-2,3-di-O-benzyl-L-gulosaccharoascorbic acid)

One drop of concentrated sulfuric acid was added to a mixture of 10.0 g of 2,3-di-O-benzyl-L-gulosaccharoascorbic acid, 13.8 g of acetic anhydride and 80 ml of dichloromethane, followed by stirring at room temperature for 15 hours.

Then, the mixture was evaporated under reduced pressure. The residue was subjected to silica gel column chromatography (solvent; dichloromethane and methanol=95:5) to yield 3.73 g of 5-O-acetyl-2,3-di-O-benzyl-L-gulosaccharoascorbic acid.

Yield: 33.5%. Melting point: 107°–110° C. (recrystallized from dichloromethane and hexane (=1:3)).
IR (KBr)cm$^{-1}$ 3300–2800, 1770, 1755, 1730, 1670.
$^1$H-NMR (CDCl$_3$) δ1.99(s, 3H), 5.05–5.23(m, 5H), 5.43(d, 1H, J=2 Hz), 7.05–7.40(m, 10H), 7.95(br, CO$_2$H). Elementary analysis (%). Calcd. for C$_{22}$H$_{20}$O$_8$: C, 64.07; H, 4.89. Found: C, 64.22; H, 4.86.

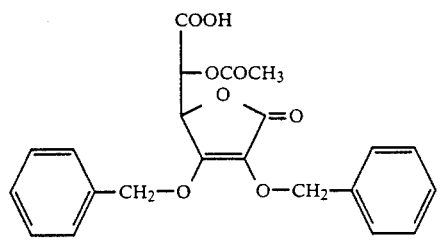

EXAMPLE 54

(n-dodecanethiolester of 5-O-acetyl-2,3-di-O-benzyl-D-glucosaccharoascorbic acid)

1.31 g of the title compound was produced from 2.20 g of 5-O-acetyl-2,3-di-O-benzyl-D-glucosaccharoascorbic acid and 1.08 g of n-dodecanethiol by a similar method to Example 44.

Yield: 41.2%. Melting point: 42°–43° C.
IR (KBr)cm$^{-1}$ 1770, 1760, 1690, 1670.
$^1$H-NMR (CDCl$_3$) δ0.88(t, 3H), 1.10–1.65(m, 20H), 2.16(s, 3H), 2.74(t, 2H, J=7 Hz), 5.00–5.15(m, 3H), 5.20(s, 2H), 5.71(d, 1H, J=3 Hz), 7.13–7.42(m, 10H). Elementary analysis (%). Calcd. for C$_{34}$H$_{44}$O$_7$S: C, 68.43; H, 7.43. Found: C, 68.50; H, 7.31.

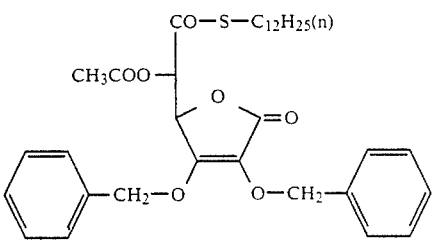

EXAMPLE 55

(n-dodecanethiolester of 2,3-di-O-benzyl-D-glucosaccharoascorbic acid)

0.98 g of the title compound (oil) was produced from 1.20 g of n-dodecanethiolester of 5-O-acetyl-2,3-di-O-benzyl-D-glucosaccharoascorbic acid produced in accordance with Example 54 by a similar method to Example 44.

Yield: 87.9%.
IR (liq. film)cm$^{-1}$ 3600–3200, 1760, 1680.
$^1$H-NMR (CDCl$_3$) δ0.88(t, 3H), 1.00–1.60(m, 20H), 2.72(m, 2H), 3.26(d, OH, J=7 Hz), 4.67(dd, 1H, J=7, 2 Hz), 5.00–5.16(m, 5H), 7.07–7.40(m, 10H). Elementary analysis (%). Calcd. for C$_{32}$H$_{42}$O$_6$S: C, 69.28; H, 7.63. Found: C, 69.30, H, 7.43.

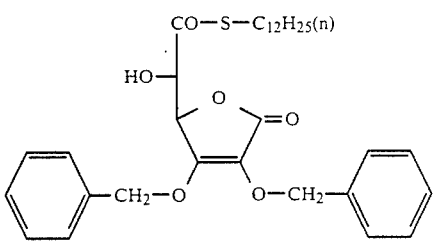

EXAMPLE 56

(methanethiolester of 5-O-acetyl-2,3-di-O-benzyl-D-glucosaccharoascorbic acid)

1.32 g of the title compound was produced from 2.20 g of 5-O-acetyl-2,3-di-O-benzyl-D-glucosaccharoascorbic acid and 0.48 g of sodium thiomethoxide by the by a similar method to Example 44.

Yield: 56.0%. Melting point: 78°–81° C.
IR (KBr)cm$^{-1}$ 1760, 1680.

$^1$H-NMR (CDCl$_3$) δ2.12(s, 3H), 2.16(s, 3H), 5.11(m, 3H), 5.18(s, 2H), 5.75(d, 1H, J=3 Hz), 7.10-7.40(m, 10H). Elementary analysis (%). Calcd. for C$_{23}$H$_{22}$O$_7$S: C, 62.43; H, 5.01. Found: C, 62.34; H, 4.85.

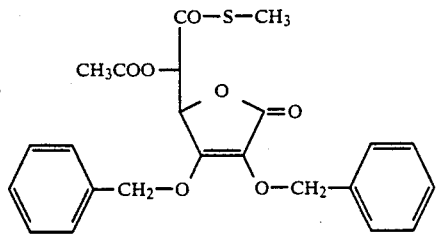

EXAMPLE 57

(methanethiolester of 2,3-di-O-benzyl-D-glucosaccharoascorbic acid)

0.82 g of the title compound was produced from 1.00 g of methanethiolester of 5-O-acetyl-2,3-di-O-benzyl-D-glucosaccharoascorbic acid produced in accordance with Example 56 by a similar method to Example 43.

Yield: 90.6%. Melting point: 87°-88° C.

IR (KBr)cm$^{-1}$ 3600-3200, 1760, 1670.

$^1$H-NMR (CDCl$_3$) δ2.08(t, 3H), 3.55(d, OH, J=7 Hz), 4.70(dd, 1H, J=7, 3 Hz), 5.00-5.16(m, 5H), 7.05-7.40(m, 10H). Elementary analysis (%). Calcd. for C$_{21}$H$_{20}$O$_6$S: C, 62.99; H, 5.03. Found: C, 62.95; H, 4.93.

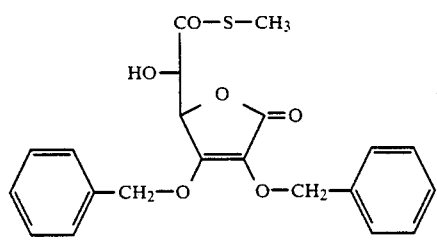

EXAMPLE 58

(methanethiolester of 5-O-acetyl-3-O-benzyl-2-O-octadecyl-D-glucosaccharoascorbic acid)

0.44 g of the title compound was produced from 0.85 g of 5-O-acetyl-3-O-benzyl-2-O-octadecyl-D-glucosaccharoascorbic acid produced in accordance with Example 40 and 0.17 g of sodium thiomethoxide by a similar method to Example 44.

Yield: 49.2%. Melting point: 63.5°-65° C. (from hexane).

IR (KBr)cm$^{-1}$ 1780, 1760, 1690, 1675.

$^1$H-NMR (CDCl$_3$) δ0.88(t, 3H), 1.05-1.75(m, 32H), 2.16(s, 3H), 2.18(s, 3H), 4.05(t, 2H, J=6 Hz), 5.11(d, 1H, J=3 Hz), 5.45(s, 2H), 5.75(d, 1H, J=3 Hz), 7.36(s, 5H). Elementary analysis (%). Calcd. for C$_{34}$H$_{52}$O$_7$S: C, 67.52; H, 8.67. Found: C, 67.78; H, 8.64.

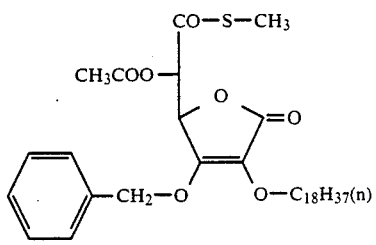

EXAMPLE 59

(methanethiolester of 3-O-benzyl-2-O-octadecyl-D-glucosaccharoascorbic acid)

0.32 g of the title compound was produced from 0.40 g of methanethiolester of 5-O-acetyl-3-O-benzyl-2-O-octadecyl-D-glucosaccharoascorbic acid produced in accordance with Example 60 by a similar method to Example 45.

Yield: 86.0%. Melting point: 54.5°-56° C. (from hexane).

IR (KBr)cm$^{-1}$ 3550-3300, 1765, 1675.

$^1$H-NMR (CDCl$_3$) δ0.88(t, 3H), 1.10-1.80(m, 32H), 2.16(s, 3H), 3.20(d, OH, J=7 Hz), 4.06(t, 2H, J=7 Hz), 4.69(dd, 1H, J=7,3 Hz), 5.11(d, 1H, J=3 Hz), 5.41(s, 2H), 7.35(s, 5H). Elementary analysis (%). Calcd. for C$_{32}$H$_{50}$O$_6$S: C, 68.29; H, 8.95. Found: C, 68.50; H, 8.99.

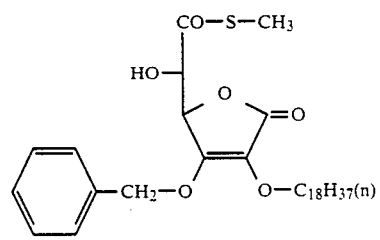

EXAMPLE 60

(n-octadecanethiolester of 5-O-acetyl-3-O-benzyl-2-O-octadecyl-D-glucosaccharoascorbic acid)

0.32 g of the title compound was produced from 0.50 g of 5-O-acetyl-3-O-benzyl-2-O-octadecyl-D-glucosaccharoascorbic acid produced in accordance with Example 38 and 0.25 g of n-octadecyl mercaptan by a similar method to Example 44.

Yield: 43.6%. Melting point: 67°-67.5° C. (from hexane).

IR (KBr)cm$^{-1}$ 1775, 1750, 1685, 1670.

$^1$H-NMR (CDCl$_3$) δ0.88(t, 3H), 1.05-1.35(m, 64H), 2.17(s, 3H), 2.77(t, 2H, J=7 Hz), 4.03(t, 2H, J=7 Hz), 5.10(d, 1H, J=3 Hz), 5.45(s, 2H), 5.72(d, 1H, J=3 Hz), 7.36(s, 5H). Elementary analysis (%). Calcd. for C$_{51}$H$_{86}$O$_7$S: C, 72.64; H, 10.28. Found: C, 72.54; H, 10.24.

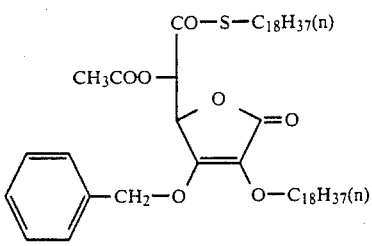

EXAMPLE 61

(n-octadecanethiolester of 3-O-benzyl-2-O-octadecyl-D-glucosaccharoascorbic acid)

0.16 g of the title compound was produced from 0.25 g of 5-O-acetyl-3-O-benzyl-2-O-octadecyl-D-glucosaccharoascorbic acid produced in accordance with Example 60 by a similar method to Example 43.

Yield: 67.5%. Melting point: 81°-82° C. (from dichloromethane-hexane=1:10).

IR (KBr)cm$^{-1}$ 3500–3300, 1760, 1670, 1645.

$^1$H-NMR (CDCl$_3$) δ0.88(t, 3H), 1.12–1.70(m, 64H), 2.78(m, 2H), 4.15(br, OH), 4.04(t, 2H, J=7 Hz), 4.65(m, 1H), 5.09(d, 1H, J=2 Hz), 5.42(s, 2H), 7.35(s, 5H). Elementary analysis (%). Calcd. for C$_{49}$H$_{84}$O$_6$S: C, 73.45; H, 10.57. Found: C, 73.66; H, 10.51.

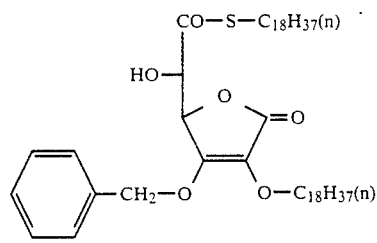

EXAMPLE 62

(n-octadecanethiolester of 5-O-acetyl-2,3-di-O-methyl-D-glucosaccharoascorbic acid)

1.04 g of the title compound was produced from 0.70 g of 5-O-acetyl-2,3-O-di-O-methyl-D-glucosaccharoascorbic acid produced in accordance with Example 50 and 0.77 g of n-octadecyl mercaptan by a similar method to Example 44.

Yield: 73.3%. Melting point: 48°-49° C. (from methanol).

IR (KBr)cm$^{-1}$ 1780, 1760, 1685, 1670.

$^1$H-NMR (CDCl$_3$) δ0.88(t, 3H), 1.05–1.70(m, 32H), 2.21(s, 3H), 2.88(t, 2H, J=7 Hz), 3.84(s, 3H), 4.13(s, 3H), 5.02(d, 1H, J=2 Hz), 5.69(d, 1H, J=2 Hz). Elementary analysis (%). Calcd. for C$_{28}$H$_{48}$O$_7$S: C, 63.60; H, 9.15. Found: C, 63.76; H, 9.02.

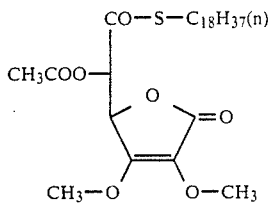

EXAMPLE 63

(n-octadecanethiolester of 2,3-di-O-methyl-D-glucosaccharoascorbic acid)

0.49 g of the title compound was produced from 0.78 g of n-octadecanethiolester of 5-O-acetyl-2,3-di-O-methyl-D-glucosaccharoascorbic acid produced in accordance with Example 62 by a similar method to Example 43.

Yield: 68.0%. Melting point: 76.5°-77° C. (from dichloromethane-hexane=1:5).

IR (KBr)cm$^{-1}$ 3530, 1775, 1680, 1655.

$^1$H-NMR (CDCl$_3$) δ0.88(t, 3H), 1.10–1.60(m, 32H), 2.92(t, 2H, J=7 Hz), 3.44(d, OH, J=7 Hz), 3.84(s, 3H), 4.10(s, 3H), 4.66(dd, 1H, J=7,3 Hz), 5.05(d, 1H, J=3 Hz). Elementary analysis (%). Calcd. for C$_{26}$H$_{46}$O$_6$S: C, 64.16; H, 9.53. Found: C, 64.30; H, 9.40.

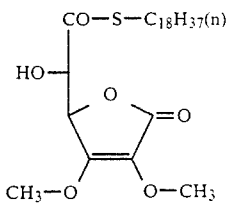

EXAMPLE 64

(n-octadecanethiolester of 2,5-di-O-acetyl-3-O-benzyl-D-glucosaccharoascorbic acid)

0.30 g of the title compound was produced from 0.30 g of 2,5-di-O-acetyl-3-O-benzyl-D-glucosaccharoascorbic acid produced in accordance with Example 52 and 0.24 g of n-octadecyl mercaptan by a similar method to Example 44.

Yield: 57.6%. Melting point: 92°-93° C.

IR (KBr)cm$^{-1}$ 1790, 1780, 1745, 1700, 1670.

$^1$H-NMR (CDCl$_3$) δ0.87(t, 3H), 1.10–1.70(m, 32H), 2.19(s, 3H), 2.21(s, 3H), 2.76(t, 2H, J=7 Hz), 5.31(m, 3H), 5.81(d, 1H, J=3 Hz), 7.35(s, 5H). Elementary analysis (%). Calcd. for C$_{35}$H$_{52}$O$_8$S: C, 66.43; H, 8.28. Found: C, 66.77; H, 8.35.

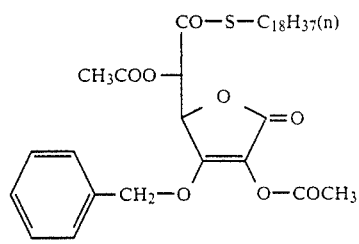

EXAMPLE 65

(n-octadecanethiolester of
3-O-benzyl-D-glucosaccharoascorbic acid)

0.071 g of the title compound was produced from 0.110 g of n-octadecanethiolester of 2,5-di-O-acetyl-3-O-benzyl-D-glucosaccharoascorbic acid produced in accordance with Example 64 by a similar method to Example 43.

Yield: 74.4%. Melting point: 98°-99° C.

IR (KBr)cm$^{-1}$ 3600-3300, 1740, 1690.

$^1$H-NMR (CDCl$_3$) δ0.88(t, 3H), 1.10-1.70(m, 32H), 2.80(m, 2H), 3.30(br, OH), 4.67(m, 1H), 5.13(d, 1H, J=2 Hz), 5.28(br, OH), 5.45(s, 2H), 7.35(s, 5H). Elementary analysis (%). Calcd. for C$_{31}$H$_{48}$O$_6$S: C, 67.85; H, 8.82. Found: C, 67.95; H, 8.86.

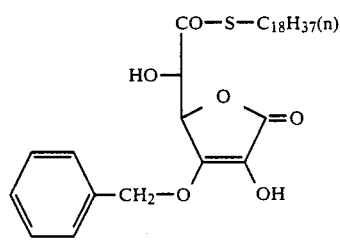

EXAMPLE 66

(n-octadecanethiolester of
3-O-benzyl-2-O-methoxycarbonylmethyl-D-glucosaccharoascorbic acid)

0.200 g of n-octadecanethiolester of 3-O-benzyl-D-glucosaccharoascorbic acid produced in accordance with Example 65 was suspended in 5 ml of dimethylsulfoxide. To this suspension was added 0.053 g of potassium carbonate, and further, added 0.053 g of methyl bromoacetate, followed by stirring at room temperature for 2 hours.

Then, the reaction mixture was diluted with 30 ml of water, extracted with dichloromethane three times. The extract was washed with water (twice), dried with sodium sulfate and evaporated under reduced pressure. The residue was subjected to silica gel column chromatography (solvent; ethyl acetate: hexane=1:4). The obtained product was recrystallized to yield 0.200 g of n-octadecanethiolester of 3-O-benzyl-2-O-methoxycarbonylmethyl-D-glucosaccharoascorbic acid.

Yield: 88.4%. Melting point: 65°-67° C.

IR (KBr)cm$^{-1}$ 3600-3300, 1775, 1680, 1660.

$^1$H-NMR (CDCl$_3$) δ0.88(t, 3H), 1.10-1.70(m, 32H), 2.78(s, 2H), 3.20(d, OH, J=8 Hz), 3.77(s, 3H), 4.65(dd, 1H, J=8,2 Hz), 4.77(s, 2H), 5.13(d, 1H, J=2 Hz), 5.58(d, 1H, J=12 Hz), 5.62(d, 1H, J=12 Hz), 7.35(s, 5H). Elementary analysis (%). Calcd. for C$_{34}$H$_{52}$O$_8$S: C, 65.78; H, 8.44. Found: C, 65.57; H, 8.57.

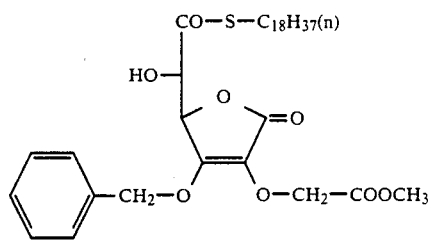

EXAMPLE 67

(n-octadecanethiolester of
3-O-benzyl-2-O-(4-chlorobenzyl)-D-glucosaccharoascorbic acid)

0.105 g of the title compound was produced from 0.250 g of n-octadecanethiolester of 3-O-benzyl-D-glucosaccharoascorbic acid produced in accordance with Example 65 and 0.095 g of 4-chlorobenzyl chloride, by a similar method to Example 66.

Yield: 34.2%. Melting point: 64°-65° C. (from hexane).

IR (KBr)cm$^{-1}$ 3480, 1770, 1680, 1665.

$^1$H-NMR (CDCl$_3$) δ0.88(t, 3H), 1.10-1.70(m, 32H), 2.75(m, 2H), 3.17(d, OH, J=7 Hz), 4.66(dd, 1H, J=7,3 Hz), 5.04(s, 2H), 5.10(d, 1H, J=3 Hz), 5.18(d, 1H), 5.20(d, 1H, J=12 Hz), 7.32(s, 5H). Elementary analysis (%). Calcd. for C$_{38}$H$_{53}$O$_6$SCl: C, 67.78; H, 7.93. Found: C, 67.76; H, 7.83.

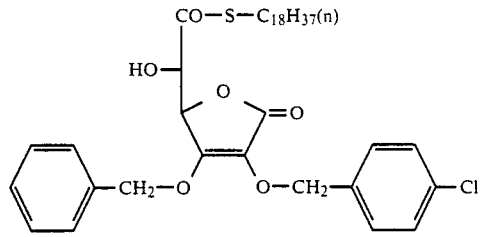

EXAMPLE 68

(n-octadecanethiolester of
3-O-benzyl-2-O-decanoyl-D-glucosaccharoascorbic acid)

0.250 g of n-octadecanethiolester of 3-O-benzyl-D-glucosaccharoascorbic acid produced in accordance with Example 65 was dissolved in 25 ml of didichloromethane. To this solution was added 0.038 g of pyridine, and further, 0.087 g of decanoyl chloride was added dropwise, followed by stirring at room temperature for 1 hours.

Then, the reaction mixture was concentrated under reduced pressure. The residue was subjected to silica gel column chromatography (solvent; ethyl acetate: hexane=1:5) to yield 0.284 g of n-octadecanethiolester of 3-O-benzyl-2-O-decanoyl-D-glucosaccharoascorbic acid.

Yield: 88.6%. Melting point: 40°-41° C.

IR (KBr)cm$^{-1}$ 3500, 1800, 1750, 1700, 1660.

$^1$H-NMR (CDCl$_3$) δ0.87(m, 6H), 1.10-1.86(m, 46H), 2.47(t, 2H, J=7 Hz), 2.75(m, 2H), 3.42(d, OH, J=7 Hz), 4.71(dd, 1H, J=7,3 Hz), 5.25(m, 3H), 7.34(s, 5H). Elementary analysis (%). Calcd. for C$_{41}$H$_{66}$O$_7$S: C, 70.05; H, 9.46. Found: C, 69.81; H, 9.64.

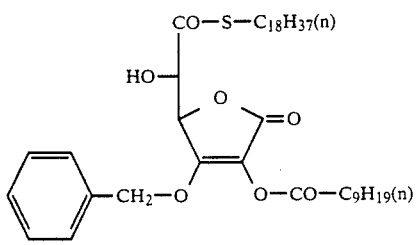

EXAMPLE 69

(n-octadecanethiolester of 5-O-acetyl-2,3-di-O-benzyl-L-gulosaccharoascorbic acid)

2.23 g of the title compound was produced from 2.00 g of 5-O-acetyl-2,3-di-O-benzyl-L-gulosaccharoascorbic acid produced in accordance with Example 53 and 1.39 g of n-octadecyl mercaptan, by a similar method to Example 44.

Yield: 67.5%. Melting point: 43°–44° C.

IR (KBr)cm$^{-1}$ 1760, 1680.

$^1$H-NMR (CDCl$_3$) δ0.88(t, 3H), 1.13–1.65(m, 32H), 2.06(s, 3H), 2.90(t, 2H, J=7 Hz), 5.05–5.20(m, 4H), 5.20(d, 1H, J=2 Hz), 5.55(d, 1H, J=2 Hz), 7.13–7.40(m, 10H). Elementary analysis (%). Calcd. for C$_{40}$H$_{56}$O$_7$S: C, 70.55; H, 8.29. Found: C, 70.83; H, 8.11.

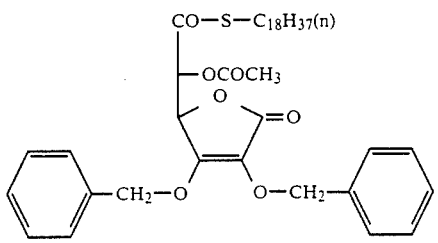

EXAMPLE 70

(n-octadecanethiolester of 2,3-di-O-benzyl-L-gulosaccharoascorbic acid)

1.12 g of the title compound was produced from 1.72 g of n-octadecanethiolester of 5-O-acetyl-2,3-di-benzyl-L-gulosaccharoascorbic acid produced in accordance with Example 69, by a similar method to Example 43.

Yield: 69.3%. Melting point: 70° C. (from ethyl acetate-hexane=1:10).

IR (KBr)cm$^{-1}$ 3550–3250, 1740, 1680, 1660.

$^1$H-NMR (CDCl$_3$) δ0.88(t, 3H), 1.10–1.65(m, 32H), 2.88(d, OH, J=9 Hz), 2.97(t, 2H, J=7 Hz), 4.44(dd, 1H, J=9,2 Hz), 5.06(d, 1H, J=2 Hz), 5.10(s, 2H), 5.17(d, 1H), 5.20(d, 1H, J=12 Hz), 7.15–7.42(m, 10H). Elementary analysis (%). Calcd. for C$_{38}$H$_{54}$O$_6$S: C, 71.44; H, 8.52. Found: C, 71.52; H, 8.44.

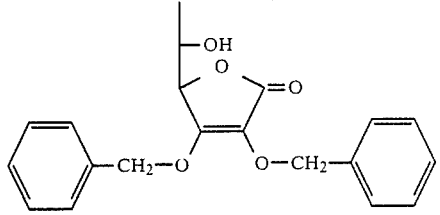

Measurement of Oxidation Potential

The oxidation potential of the compound of the present invention is measured by Cyclic Voltammetry under the following conditions;

substrate: 5 mmol/l in CH$_3$CN containing 0.1M LiClO$_4$
scan rate: 100 mV/sec
Pt electrodes The results are shown in the following Table.

TABLE

| Compound | anodic peak potentials (V vs SCE) |
|---|---|
| Example 18 | +1.26 |
| Example 20 | +1.28 |
| Example 36 | +1.15 |
| Example 48 | +1.14 |
| Control | +1.13 |

(Note) control: D-glucosaccharoascorbic acid

From the above results, it is clear that the compound of the present invention, which has at least one hydroxyl group at the 2- or 3-position, has the same level of reducing activity as the control compound.

The control compound has already been disclosed in European Patent Laid-open No. 0,228,273. It is a compound known as having the same level of reducing activity as an ascorbic acid.

What we claim is:

1. A compound represented by the formula

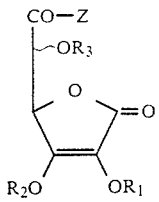

wherein R$_1$, R$_2$ and R$_3$ independently represent hydrogen, an acyl group of 1 to 18 carbon atoms which is derived from carboxylic acid, an alkyl of 1 to 24 carbon atoms, a cycloalkyl of 3 to 8 carbon atoms, an alkenyl of 2 to 24 carbon atoms, an alkynyl of 2 to 24 carbon atoms. an aralkyl of 2 to 24 carbon atoms or an aryl of 1 to 24 carbon atoms selected from carbocyclic and heterocyclic aromatic groups;

Z represents

—SR$_6$ or —OR$_7$;

$R_4$ and $R_5$ independently represent hydrogen, an alkyl of 1 to 24 carbon atoms, a cycloalkyl of 3 to 8 carbon atoms, an alkenyl of 2 to 24 carbon atoms, an alkynyl of 2 to 24 carbon atoms, an aralkyl of 2 to 24 carbon atoms or an aryl of 1 to 24 carbon atoms selected from carbocyclic and heterocyclic aromatic groups, or $R_4$ and $R_5$ may together form —$(CH_2)$—n in which n is an integer of 4 to 7;

$R_6$ represents an alkyl of 1 to 24 carbon atoms, a cycloalkyl of 3 to 8 carbon atoms, an alkenyl of 2 to 24 carbon atoms, an alkynyl of 2 to 24 carbon atoms, an aralkyl of 2 to 24 carbon atoms or an aryl of 1 to 24 carbon atoms selected from carbocyclic and heterocyclic aromatic groups;

$R_7$ represents hydrogen, an alkyl of 1 to 24 carbon atoms, a cycloalkyl of 3 to 8 carbon atoms, an alkenyl of 2 to 24 carbon atoms, an alkynyl of 2 to 24 carbon atoms, an aralkyl of 2 to 24 carbon atoms or an aryl of 1 to 24 carbon atoms selected from carbocyclic and heterocyclic aromatic groups; and ~ represents the R-configration or the S-configration;

with the proviso that when Z is —$OR_7$, $R_1$ and $R_2$ are not the same and $R_3$ is hydrogen;

or a pharmaceutically acceptable salt thereof.

2. A compound or a pharmaceutically acceptable salt as claimed in claim 1, wherein Z is

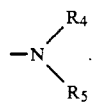

3. A compound or a pharmaceutically acceptable salt as claimed in claim 1, wherein Z is —$SR_6$.

4. A compound represented by the formula

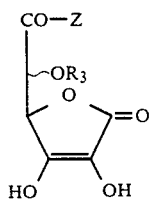

wherein Z represents

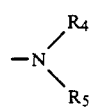

or —$SR_6$;

$R_4$ and $R_5$ independently represent hydrogen, an alkyl of 1 to 24 carbon atoms, a cycloalkyl of 3 to 8 carbon atoms, an alkenyl of 2 to 24 carbon atoms, an alkynyl of 2 to 24 carbon atoms, an aralkyl of 2 to 24 carbon atoms or an aryl of 1 to 24 carbon atoms selected from carbocyclic and heterocyclic aromatic groups, or $R_4$ and $R_5$ may together form —$(CH_2)$—n in which n is an integer of 4 to 7;

$R_6$ represents an alkyl of 1 to 24 carbon atoms, a cycloalkyl of 3 to 8 carbon atoms, an alkenyl of 2 to 24 carbon atoms, an alkynyl of 2 to 24 carbon atoms, an aralkyl of 2 to 24 carbon atoms or an aryl of 1 to 24 carbon atoms selected from carbocyclic and heterocyclic aromatic groups;

$R_3$ represents hydrogen or an acyl group of 1 to 18 carbon atoms which is derived from carboxylic acid; and ~ represents the R-configration or the S-configration;

or a pharmaceutically acceptable salt thereof.

5. A compound or a pharmaceutically acceptable salt as claimed in claim 4, wherein Z is

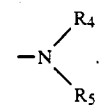

6. A compound or a pharmaceutically acceptable salt as claimed in claim 4, wherein Z is —$SR_6$.

7. A compound represented by the formula

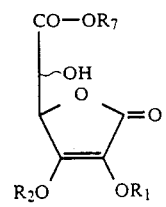

wherein $R_1$ and $R_2$ independently represent hydrogen, an alkyl of 1 to 24 carbon atoms, a cycloalkyl of 3 to 8 carbon atoms, an alkenyl of 2 to 24 carbon atoms, an alkynyl of 2 to 24 carbon atoms, an aralkyl of 2 to 24 carbon atoms or an aryl of 1 to 24 carbon atoms selected from carbocyclic and heterocyclic aromatic groups;

$R_1$ and $R_2$ are not the same;

$R_7$ represents hydrogen, an alkyl of 1 to 24 carbon atoms, a cycloalkyl of 3 to 8 carbon atoms, an alkenyl of 2 to 24 carbon atoms, an alkynyl of 2 to 24 carbon atoms, an aralkyl of 2 to 24 carbon atoms or an aryl of 1 to 24 carbon atoms selected from carbocyclic and heterocyclic aromatic groups; and ~ represents the R-configration or the S-configration;

or a pharmaceutically acceptable salt thereof.

8. A compound represented by the formula

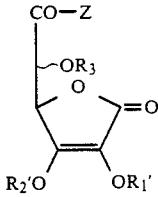

wherein Z represents

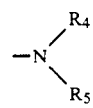

or —$SR_6$;

$R_4$ and $R_5$ independently represent hydrogen, an alkyl of 1 to 24 carbon atoms, a cycloalkyl of 3 to 8 carbon atoms, an alkenyl of 2 to 24 carbon atoms, an alkynyl of 2 to 24 carbon atoms, an aralkyl of 2 to 24 carbon atoms or an aryl of 1 to 24 carbon atoms, or $R_4$ and $R_5$ may together form $-(CH_2)-n$ in which n is an integer of 4 to 7;

$R_6$ represents an alkyl of 1 to 24 carbon atoms, a cycloalkyl of 3 to 8 carbon atoms, an alkenyl of 2 to 24 carbon atoms, an alkynyl of 2 to 24 carbon atoms, an aralkyl of 2 to 24 carbon atoms or an aryl of 1 to 24 carbon atoms selected from carbocyclic and heterocyclic aromatic groups;

$R_1'$ and $R_2'$ independently represent hydrogen or a protective group, at least one of $R_1'$ and $R_2'$ being a protective group;

$R_3$ represents a hydrogen or a protective group; and

∼ represents the R-configration or the S-configration;

or a pharmaceutically acceptable salt thereof.

9. A compound or a pharmaceutically acceptable salt as claimed in claim 8, wherein Z is

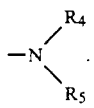

10. A compound or a pharmaceutically acceptable salt as claimed in claim 9 wherein the protective group for $R_1'$ and $R_2'$ is a benzyl group which may be substituted by methoxy, nitro, chloro, bromo or cyano, an acyl group of 1 to 18 carbon atoms which is derived from carboxylic acid or an alkoxyalkyl group; and the protective group for $R_3$ is an acyl group of 1 to 18 carbon atoms which is derived from carboxylic acid.

11. A compound or a pharmaceutically acceptable salt as claimed in claim 10, wherein the said benzyl group is benzyl, p-methoxybenzyl, o-nitrobenzyl, p-nitrobenzyl, p-chlorobenzyl, p-bromobenzyl or p-cyanobenzyl.

12. A compound as claimed in claim 10, wherein the said acyl is formyl, acetyl, propionyl, butyryl, isobutyryl, valeryl, isovaleryl, pivaloyl or benzoyl.

13. A compound or a pharmaceutically acceptable salt as claimed in claim 8, wherein Z is $-SR_6$.

14. A compound or a pharmaceutically acceptable salt as claimed in claim 13, wherein the protective group for $R_1'$ and $R_2'$ is a benzyl group which may be substituted by methoxy, nitro, chloro, bromo or cyano, an acyl group of 1 to 18 carbon atoms which is derived from carboxylic acid or an alkoxyalkyl group; and the protective group for $R_3$ is an acyl group of 1 to 18 carbon atoms which is derived from carboxylic acid.

15. A compound or a pharmaceutically acceptable salt as claimed in claim 14, wherein the said benzyl group is benzyl, p-methoxybenzyl, o-nitrobenzyl, p-nitrobenzyl, p-chlorobenzyl, p-bromobenzyl or p-cyanobenzyl.

16. A compound or a pharmaceutically acceptable salt as claimed in claim 13, wherein the said acyl is formyl, acetyl, propionyl, butyryl, isobutyryl, valeryl, isovaleryl, pivaloyl or benzoyl.

17. A compound or a pharmaceutically acceptable salt as claimed in claim 10, wherein the said alkoxyalkyl group is methoxymethyl, tert-butoxymethyl, 1-ethoxyethyl or 1-methyl-1-methoxymethyl.

18. A compound or a pharmaceutically acceptable salt as claimed in claim 14, wherein the said alkoxyalkyl group is methoxymethyl, tert-butoxymethyl, 1-ethoxyethyl or 1-methyl-1-methoxymethyl.

19. A compound or a pharmaceutically acceptable salt as claimed in claim 13, wherein $R_1'$ and $R_2'$ independently represent hydrogen or benzyl; $R_3$ represents hydrogen or an acyl group of 1 to 18 carbon atoms which is derived from carboxylic acid; and $R_6$ represents an alkyl of 1 to 24 carbon atoms or an aryl group of 1 to 24 carbon atoms selected from carbocyclic and heterocyclic aromatic groups.

20. A compound or a pharmaceutically acceptable salt as claimed in claim 19, wherein the said acyl group for $R_3$ is acetyl, and the alkyl for $R_6$ is methyl, dodecyl, octadecyl or phenyl.

21. A compound or a pharmaceutically acceptable salt as claimed in claim 1, wherein $R_1$ and $R_2$ are benzyl which may be substituted by chloro; $R_3$ represents hydrogen or acetyl; Z represents $-S-R_6$; and $R_6$ represents phenyl or an alkyl group of 1 to 18 carbon atoms.

22. A compound or a pharmaceutically acceptable salt as claimed in claim 1, which is n-octadecanethiol ester of 5-O-acetyl-2,3-di-O-benzyl-D-glucosaccharoascorbic acid.

23. A compound or a pharmaceutically acceptable salt as claimed in claim 1, wherein $R_1$ and $R_2$ independently represent hydrogen or benzyl; $R_3$ represents hydrogen or acetyl; Z represents $-NH-R_4$ or

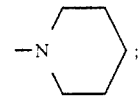

and $R_4$ represents hydrogen or an alkyl group of 1 to 18 carbon atoms.

24. A compound or a pharmaceutically acceptable salt as claimed in claim 1, wherein the salt is alkali metal salt, alkaline earth metal salt, ammonium salt, pyridinium salt or substituted ammonium salt.

* * * * *